(12) United States Patent
Minekawa et al.

(10) Patent No.: US 8,824,773 B2
(45) Date of Patent: Sep. 2, 2014

(54) DEFECT OBSERVATION METHOD AND DEFECT OBSERVATION DEVICE

(75) Inventors: Yohei Minekawa, Fujisawa (JP); Ryo Nakagaki, Kawasaki (JP); Kenji Nakahira, Fujisawa (JP); Takehiro Hirai, Ushiku (JP); Katsuhiro Kitahashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 120 days.

(21) Appl. No.: 13/515,643

(22) PCT Filed: Nov. 19, 2010

(86) PCT No.: PCT/JP2010/006784
§ 371 (c)(1),
(2), (4) Date: Aug. 6, 2012

(87) PCT Pub. No.: WO2011/074183
PCT Pub. Date: Jun. 23, 2011

(65) Prior Publication Data
US 2013/0140457 A1     Jun. 6, 2013

(30) Foreign Application Priority Data

Dec. 16, 2009  (JP) ................................ 2009-284667
Jun. 30, 2010  (JP) ................................ 2010-148486

(51) Int. Cl.
*G06K 9/00*     (2006.01)
*G06K 9/46*     (2006.01)
*G01N 23/22*    (2006.01)
*H01J 37/26*    (2006.01)
*G06T 7/00*     (2006.01)

(52) U.S. Cl.
CPC ............... *H01J 37/26* (2013.01); *G01N 23/22* (2013.01); *G06T 2207/30148* (2013.01); *G01N 2223/421* (2013.01); *G01N 2223/6116* (2013.01); *G01N 2223/6466* (2013.01); *G06T 2207/10061* (2013.01); *G06T 2207/22081* (2013.01); *G06T 7/0004* (2013.01); *G06T 2200/24* (2013.01)
USPC .......................................... 382/141; 382/190

(58) Field of Classification Search
USPC ......... 382/125, 141, 145, 149, 190, 218–220; 356/237.1–237.4; 702/183
See application file for complete search history.

(56) References Cited

U.S. PATENT DOCUMENTS 7,006,687 B2 * 2/2006 Kim .............................. 382/162
7,366,343 B2 * 4/2008 Takeuchi ....................... 382/145
(Continued)

FOREIGN PATENT DOCUMENTS

JP    2001-331784    11/2001
JP    2002-41559     2/2002
(Continued)

OTHER PUBLICATIONS

Office Action in corresponding Application No. 10-2012-7015661, dated Sep. 12, 2013.

*Primary Examiner* — Amir Alavi
(74) *Attorney, Agent, or Firm* — Antonelli, Terry, Stout & Kraus, LLP.

(57) ABSTRACT

A defect observation device including an input-output unit supplied with information of a taught defect, and information of an ideal output of the taught defect, and configured to display a processing result based upon a determined image processing parameter set; and an automatic determination unit configured to: select image processing parameter sets which are less in number than the total number of all image processing parameter sets, out of all image processing parameter sets, calculate image processing results on an input defect image, by using the selected image processing parameter sets, calculate a coincidence degree for each of the selected image processing parameter sets, estimate distribution of an index value in all image processing parameter sets from distribution of the coincidence degree for the selected image processing parameter sets, and determine an image processing parameter set to have a high coincidence degree out of all image processing parameter sets.

20 Claims, 12 Drawing Sheets

(56) References Cited

U.S. PATENT DOCUMENTS

| | | |
|---|---|---|
| 7,834,992 B2 * | 11/2010 | Yoshida et al. ............ 356/237.2 |
| 8,027,527 B2 * | 9/2011 | Shibuya et al. .............. 382/141 |
| 2001/0042705 A1 | 11/2001 | Nakagaki et al. |
| 2004/0228515 A1 | 11/2004 | Okabe et al. |
| 2009/0222753 A1 | 9/2009 | Yamaguchi et al. |
| 2013/0140457 A1 * | 6/2013 | Minekawa et al. ........... 250/307 |

FOREIGN PATENT DOCUMENTS

| | | |
|---|---|---|
| JP | 2004-47939 | 2/2004 |
| JP | 2004-294358 | 10/2004 |
| JP | 2007-198968 | 8/2007 |
| JP | 2008-116207 | 5/2008 |
| JP | 2009-103508 | 5/2009 |
| JP | 2009-210309 | 9/2009 |

* cited by examiner

DEFECT OBSERVATION METHOD AND DEFECT OBSERVATION DEVICE

This application is a 371 of PCT/JP2010/006784 filed on Nov. 19, 2010.

TECHNICAL FIELD

The present invention relates to a defect observation method and a defect observation device for observing defects or the like on a sample, and in particular to improvement of convenience in use of the defect observation method and the defect observation device.

BACKGROUND ART

In the semiconductor manufacturing process, it becomes important to immediately clear up the cause of defect generation on a semiconductor wafer in order to improve the yield. Under the existing circumstances, analysis of a defect is conducted by using a defect inspection device and a defect observation device on the spot of semiconductor manufacturing.

The defect inspection device is a device for observing a wafer by using an optical means or an electron beam and outputting location coordinates of a detected defect. In the defect inspection device, it is important to process a wide range fast. Therefore, the image data quantity is reduced by making the pixel size of an acquired image as large as possible (i.e., making the resolution low). In many cases, therefore, it is difficult to discriminate the kind of a defect (defect kind) in detail, even if existence of the defect can be confirmed from the detected image of the low resolution.

Therefore, a defect observation device is used. The defect observation device is a device for imaging coordinates of a defect on the wafer with high resolution by using output information of the defect inspection device and outputting an image. The semiconductor manufacturing process shrinks in size and consequently the defect size also reaches an order of several tens nm. For observing a defect in detail, therefore, a resolution of an order of several nm is needed.

In recent years, therefore, a defect observation device (review SEM) using a scanning electron microscope is widely used. The review SEM has an ADR (Automatic Defect Review) function of automatically collecting high resolution images of defects (defect images) on a wafer by using defect coordinates which are output by the defect inspection device.

In recent years, the throughput of the ADR of the review SEM has been improved. Therefore, it is desired to automatize the work of discriminating the defect kind on the basis of a large amount of collected defect images. The review SEM mounts an ADC (Automatic Defect Classification) function of automatically discriminating a defect kind on the basis of defect images and classifying the defect. As for the conventional art relating to the ADC, there is, for example, a technique disclosed in Patent Literature 1 described later.

CITATION LIST

Patent Literatures

Patent Literature 1: JP-A-2001-331784
Patent Literature 2: JP-A-2004-294358

SUMMARY OF INVENTION

Technical Problem

The ADC calculates values (feature quantities) which quantize a feature of a defect, from defect images on the basis of the size, height, and shape of the defect and position relations of the defect to its peripheral circuit pattern, and classifies the defect kind by using those kinds of information. When conducting the calculation of the feature quantities, a plurality of kinds of image processing, such as defect recognition processing for extracting a defect area in a defect image, interconnection recognition processing for recognizing a circuit pattern around the defect (an interconnection region), and unevenness decision processing for making a decision as to the situation of unevenness on the surface of the defect, are executed. The feature quantities are calculated by using results (intermediate results) of these kinds of image processing.

In these kinds of image processing, it is usually necessary to specify image processing parameters. The image processing parameters depend upon contents of an image processing algorithm. For example, when recognizing a recognition object by utilizing its lightness on an image, a threshold (binarization threshold) for the lightness can be mentioned as the image processing parameter. In processing for recognizing a body by using images of a plurality of kinds jointly, mixture ratios which are composition ratios of those images can be mentioned. Usually, a plurality of image processing parameters are needed for one image processing algorithm in many cases. If the setting of image processing parameters is changed, therefore, an intermediate result of each image processing and a final recognition result change, even if the same image processing algorithm is used.

Not only a plurality of image processing parameters are prepared, but also a plurality of image processing algorithms themselves are prepared, and a suitable method is selected according to an image to be processed and suitable image processing parameters are given for the selected method to conduct processing, in some cases. In other words, in these image processing algorithms, the number and kinds of contained parameters differ from algorithm to algorithm and a final recognition result changes according to the kind of the utilized image processing algorithm and setting values of its image processing parameters. In the processing of the above-described ADC, the size of the recognized defect area and values of obtained feature quantities are changed and the classification precision of the ADC is changed by changing setting of image processing parameters and image processing algorithms even in the case where the same defect image is used.

Under the existing circumstances, setting of a combination (image processing parameter set) of image processing parameter values used to calculate feature quantities requires trial and error conducted by an expert.

Taking processing (defect recognition) for extracting a defect area from an image which is needed as a first step in the feature quantity calculation as an example, its concrete procedure is as follows.

(1) With respect to each of defect images, a result of an area extracted by the image processing parameter set which is set is confirmed.

(2) If the extracted area is not desirable, the image processing parameter set is set again and extraction of the defect area is done over again.

(3) The works of (1) and (2) are conducted repeatedly until desirable results are obtained with respect to all defect images, and the image processing parameter set is determined.

These works require skill of a high order for the device. Much time and trouble are required of a person who does not use the device so frequently or a beginner for the device, resulting in a large barrier to use of the device.

In order to remove the barrier and facilitate the use of the device, for example, a method of displaying a list of image processing parameter sets which are set and their results to facilitate visual understanding is proposed in Patent Literature 1. According to this technique, a list of processing results calculated for all image processing parameter sets with respect to all defect images is displayed.

If the number of image processing parameters to be set is large, however, the number of the image processing parameter sets becomes enormously large. The user is requested to select an optimum image processing parameter set out of displayed processing results for an enormously large number of image processing parameter sets. Furthermore, for outputting a list of image processing results in all parameter sets, it is necessary to conduct image processing on all parameter sets and a long time is needed until the list is output. In addition, there is a problem that skill of a high order is still needed when selecting an optimum image processing parameter set.

Therefore, an object of the present invention is to provide a defect observation method and a defect observation device which make it possible to solve the problems and conduct the work of setting the image processing parameters required to classify defect kinds easily and fast. As a conventional art relating to facilitation of the parameter setting work, for example, there is a technique disclosed in the Patent Literature 2.

The above described and other objects and novel features of the present invention will be clarified from description in the present specification and accompanying drawings.

Solution to Problem

Outlines of representative inventions among inventions disclosed in the present application will now be described briefly.

(1) A defect observation method for observing a defect of a sample, including the steps of picking up a plurality of defect images by using an electron microscope on the basis of previously detected defect coordinates of a sample, processing a defect image for teaching (hereafter referred to as teaching defect image) selected out of the plurality of picked up defect images, by using respective conditions of a first plurality of image processing parameter sets which are previously set, and extracting a plurality of defect areas respectively corresponding to the first plurality of image processing parameter sets, comparing an ideal defect area which is set to correspond to the selected teaching defect image with the extracted plurality of defect areas and calculating a coincidence degree for each of the plurality of defect areas, calculating an estimated value of coincidence degree with respect to each of a second plurality of image processing parameter sets different from the first plurality of image processing parameter sets which are previously set, by using the coincidence degree calculated for each of the plurality of defect areas, selecting one or a plurality of image processing parameter sets out of the first plurality of image processing parameter sets which are previously set and the second plurality of image processing parameter sets on the basis of the calculated plurality of coincidence degrees and estimated values of coincidence degree, and conducting image processing on the plurality of defect images picked up with the electron microscope by using the selected image processing parameter set and classifying the defect of the sample on the basis of the defect images subjected to the image processing.

(2) The defect observation method described in (1), wherein the first plurality of image processing parameter sets which are previously set are less in number than the second plurality of image processing parameter sets.

(3) A defect observation method for observing a defect of a sample, including the steps of picking up a plurality of defect images and non-defective article images by using an electron microscope on the basis of previously detected defect coordinates of a sample, processing a teaching interconnection image selected out of the picked up non-defective article images, by using respective conditions of a first plurality of combinations of image processing parameter sets and image processing algorithms which are previously set, and extracting a plurality of interconnection areas respectively corresponding to the first plurality of image processing parameter sets and image processing algorithms, comparing an ideal interconnection area which is set to correspond to the selected teaching interconnection image with the extracted plurality of interconnection areas and calculating a coincidence degree for each of the plurality of interconnection areas, calculating an estimated value of coincidence degree with respect to each of a second plurality of combinations of image processing parameter sets and image processing algorithms different from the first plurality of combinations of image processing parameter sets and image processing algorithms which are previously set, by using the coincidence degree calculated for each of the plurality of interconnection areas, selecting one or a plurality of image processing parameter sets and image processing algorithms out of the first plurality of combinations of image processing parameter sets and image processing algorithms which are previously set and the second plurality of combinations of image processing parameter sets and image processing algorithms on the basis of the calculated plurality of coincidence degrees and estimated values of coincidence degree, and conducting image processing on the plurality of defect images picked up with the electron microscope by using the selected image processing parameter sets and image processing algorithms and classifying the defect of the sample on the basis of the defect images subjected to the image processing.

(4) A defect observation method in a defect observation device including an image acquisition unit for acquiring a defect image of a sample, a storage unit, and an input/output unit, an operation unit which is supplied with image information from the image acquisition unit and which conducts image processing for recognizing a defect on the sample and classifying a defect kind on the image information on the sample by using a previously set image processing parameter set, and an automatic determination unit for automatically determining setting candidates of the image processing parameter set, the defect observation method including the steps of selecting, in the input/output unit, one or a plurality of representative defects, inputting, in the operation unit, ideal outputs for the representative defects of the image processing, calculating coincidence degrees between output results obtained by conducting the image processing on the representative defects in a small number of image processing parameter sets and the ideal outputs, calculating estimated values of coincidence degrees with respect to image processing parameter sets which are not included in the small number of image processing parameter sets, on the basis of the coincidence degrees, determining one set or a plurality of sets of setting candidates of the image processing parameter set on the basis of the estimated values of coincidence degrees and the coincidence degrees, and displaying, in the input/output unit, the image processing parameter set of the setting candidate and output results obtained by conducting the image processing on the representative defects in the image processing parameter set of the setting candidate.

(5) A defect observation device including an image acquisition means for irradiating a sample with an electron beam, detecting primary electrons reflected by the sample and/or secondary electrons generated by the sample, and acquiring an image, and a signal processing means for processing the image acquired by the image acquisition means, the signal processing means including an input/output unit for accepting instruction information given by a user, a defect information storage unit for storing a plurality of defect images acquired by the image acquisition means and outputting a teaching defect image selected out of the plurality of defect images on the basis of the instruction information accepted by the input/output unit, a defect recognition unit for processing a teaching defect image which is output from the defect information storage unit, by using respective conditions of a first plurality of image processing parameter sets which are previously set, and extracting a plurality of defect areas respectively corresponding to the first plurality of image processing parameter sets, a coincidence degree calculation unit for comparing the plurality of defect areas extracted in the defect recognition unit with an ideal defect area which is set on the basis of the instruction information accepted by the input/output unit and calculating a coincidence degree for each of the plurality of defect areas, a coincidence degree estimation unit for calculating an estimated value of coincidence degree with respect to each of a second plurality of image processing parameter sets different from the first plurality of image processing parameter sets which are previously set, by using the coincidence degree calculated for each of the plurality of defect areas by the coincidence degree calculation unit, a parameter determination unit for selecting one or a plurality of image processing parameter sets out of the first plurality of image processing parameter sets which are previously set and the second plurality of image processing parameter sets on the basis of the plurality of coincidence degrees and estimated values of coincidence degree calculated in the coincidence degree calculation unit and the coincidence degree estimation unit, a feature quantity calculation unit for determining defect areas of the plurality of defect images acquired by the image acquisition means and calculating feature quantities in the defect areas of the plurality of defect images, and a classification unit for classifying a defect of the sample on the basis of the feature quantities calculated by the feature quantity calculation unit.

(6) The defect observation method described in (1), wherein the ideal defect area is an area selected out of image processing results processed by using image processing parameter sets which are specified by a user or selected randomly.

(7) The defect observation method described in (1), wherein the teaching defect image is an image selected automatically by using information of a defect kind based upon the plurality of picked up defect images as reference.

(8) The defect observation device described in (5), wherein the input/output unit further displays a list of defect recognition results based on a plurality of image processing parameter sets which are specified by a user or selected randomly and accepts one or a plurality of defect recognition results with respect to one taught defect selected out of the defect recognition results displayed as the list, as instruction information for setting the ideal defect area.

(9) The defect observation device described in (8), wherein the input/output unit displays a list of defect recognition results based on a plurality of image processing parameter sets which are specified by a user or selected randomly, in order of the feature quantity or a recognized area size.

In particular, the input-output unit, and an automatic determination unit for an image processing parameter set constituted to include the coincidence degree calculation unit, the coincidence degree estimation unit and the parameter determination unit, in the defect observation device have the following functions, respectively.

For example, the input-output unit is capable of having functions such as 1) inputting information of evaluation defect images (taught defects) for automatically determining an image processing parameter set, selected out of a large number of automatically collected defect images and ideal output results (ideal outputs) obtained in the case where image processing is executed on the evaluation images, and 2) displaying processing results based upon the determined image processing parameter set.

Furthermore, the automatic determination unit for image processing parameter set is capable of having functions such as 1) calculating image processing results for a defect image which is input, by using image processing parameter sets which are less in number than the total number of all image processing parameter sets, selected out of all image processing parameter sets, 2) calculating an index value (coincidence degree) which represents a degree of coincidence between an image processing result and an ideal output for each of the selected image processing parameter sets, 3) estimating distribution of the index value in all image processing parameter sets from distribution of the coincidence degree for the selected image processing parameter sets, and 4) determining an image processing parameter set having a high coincidence degree out of all image processing parameter sets.

Advantageous Effects of Invention

According to the present invention, it is possible to provide a defect observation method and a defect observation device which make it possible to solve the above-described problems and conduct the work of setting the image processing parameters required to classify defect kinds easily and fast.

DESCRIPTION OF EMBODIMENTS

Figure 1:
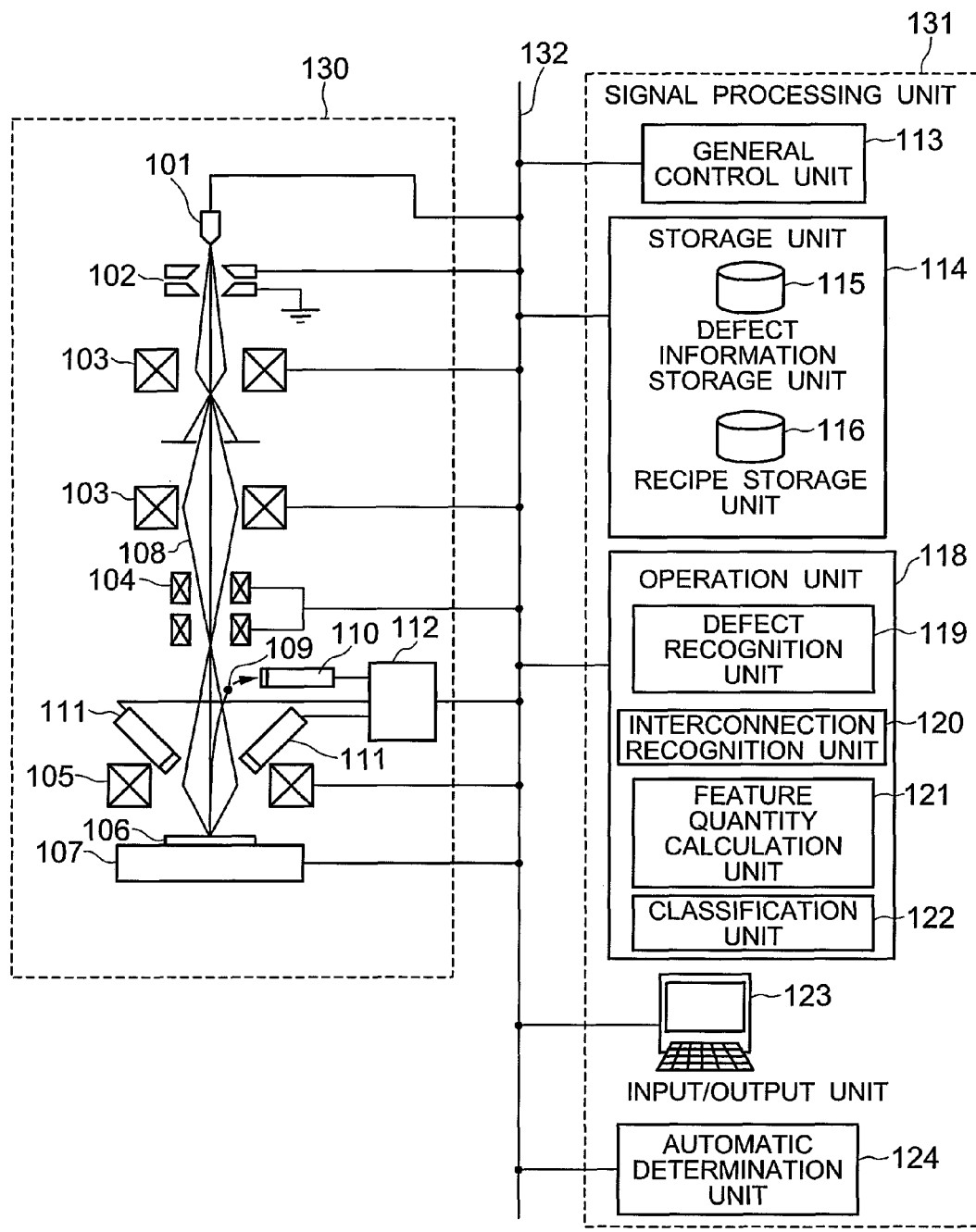
FIG. 1 is a configuration diagram showing a configuration of a defect observation device according to an embodiment 1 of the present invention.

Hereafter, embodiments of the present invention will be described in detail with reference to the drawings. By the way, throughout all drawings for describing the embodiments, the same members are denoted by like reference numerals in principle and repeated description of them will be omitted.

Embodiment 1

A first embodiment of a defect observation method and a defect observation device according to the present invention will now be described with reference to FIGS. 1 to 3.

A defect observation device shown in FIG. 1 is composed of a SEM image acquisition unit 130 and a signal processing unit 131, and a bus 132 is coupled between the SEM image acquisition unit 130 and the signal processing unit 131.

The SEM image acquisition unit 130 is suitably composed of an electron source 101 for generating primary electrons 108, an acceleration electrode 102 for accelerating the primary electrons, a focusing lens 103 for converging the primary electrons, a deflector 104 for conducting two-dimensional scanning and deflection on the primary electrons, an objective lens 105 for focusing the primary electrons onto a sample 106, a stage 107 mounting the sample 106 and capable of moving in an XY plane, a detector 110 for detecting secondary electrons 109 generated from the sample, a detector 111 for detecting primary electrons reflected by a sample face, and a digitization means 112 for digitizing (A/D converting) a detected signal. These components are connected to a general control unit 113 which controls the whole defect observation device, through the bus 132. By the way, an example in which there are three detectors is shown here. However, this is not restrictive, but various changes are possible.

The signal processing unit 131 is configured to suitably include the general control unit 113, an operation unit 118, a storage unit 114, an input/output unit 123 composed of devices, such as a keyboard, a mouse, a pen-type input device, and a touch panel, for giving instructions to the defect observation device, and a monitor or a printer for outputting data from the defect observation device, and an automatic determination unit 124 for automatically determining an image processing parameter set and the like. They are connected to each other by the bus 132.

The operation unit 118 is configured to suitably include a defect recognition unit 119 for recognizing an area of a defect by suitably using a defect image and a non-defective article image, an interconnection recognition unit 120 for recognizing an interconnection in a circuit pattern on the basis of the non-defective article image, a feature quantity calculation unit 121 for calculating feature quantities on the basis of recognition results obtained from the defect recognition unit 119, the interconnection recognition unit 120 or the like, and a classification unit 122 for discriminating a defect kind on the basis of the feature quantities calculated by the feature quantity calculation unit 121. In the example in FIG. 1, only the defect recognition unit 119 and the interconnection recognition unit 120 are shown as means which output intermediate results for feature quantity calculation. However, the means are not restricted to them, but other means which supply operation results usable for feature quantity calculation may be suitably used. A configuration in which the automatic determination unit 124 is included in the operation unit 118 may also be used.

The storage unit 114 is configured to suitably include a defect information storage unit 115 for storing data of a picked up image and information concerning a defect, such as defect coordinates, detected by another inspection device, and a recipe storage unit 116 for storing various conditions of an electro-optic system at the time of image pickup and image processing parameters, such as a binarization threshold and a mixture ratio, utilized when calculating feature quantities, as a recipe.

An automatic adjustment method of image processing parameters according to the present invention will now be described with reference to FIGS. 2 and 3.

Figure 2:
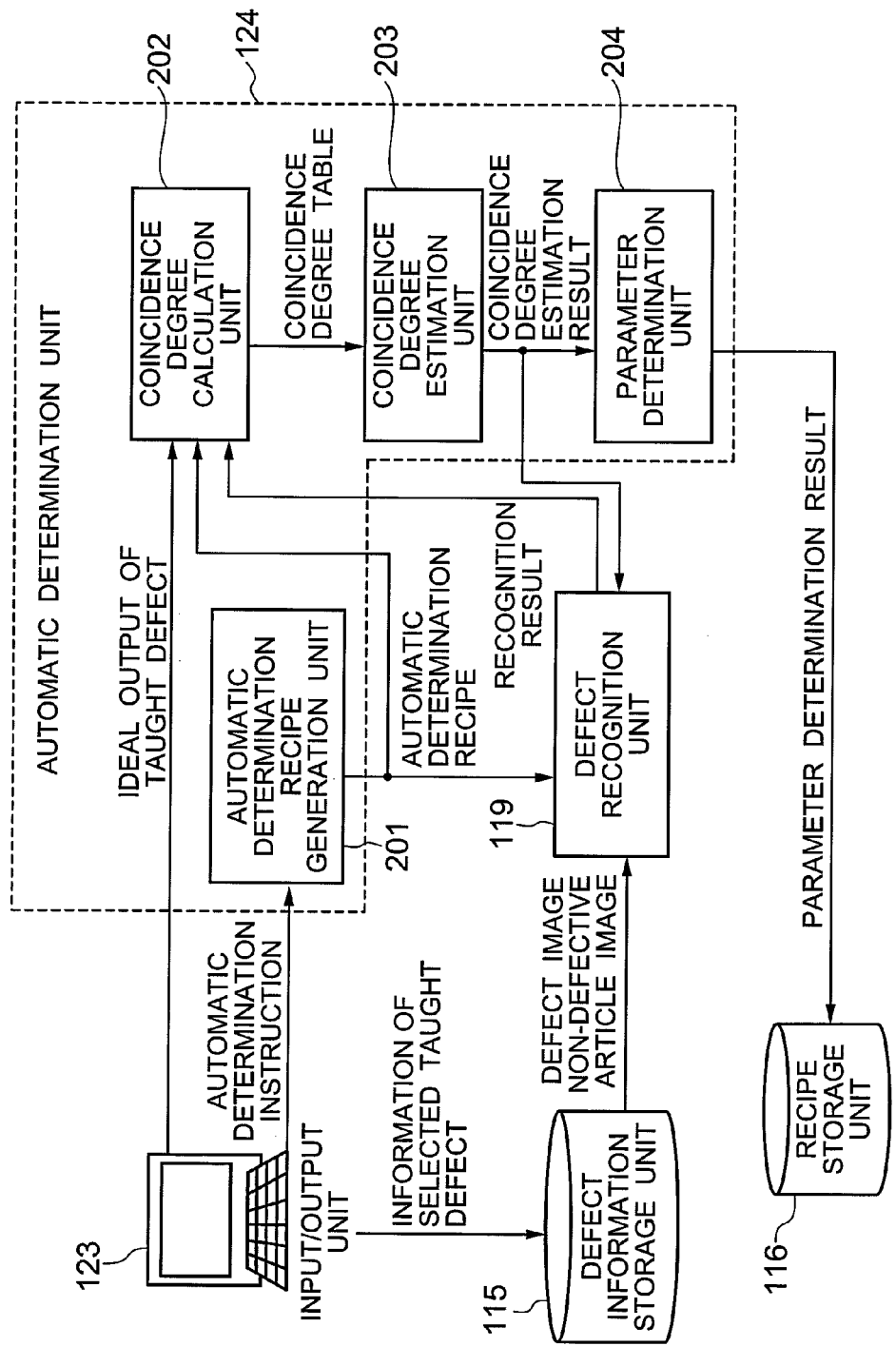
FIG. 2 is a diagram showing a device configuration and a data flow in an automatic determination unit in the defect observation device according to the embodiment 1 of the present invention.

FIG. 2 shows a device configuration and a data flow in the automatic determination unit. The automatic determination unit 124 is configured to suitably include an automatic determination recipe generation unit 201 for generating a plurality of automatic determination recipes (which indicate an image processing parameter set, in the present embodiment) used for automatic determination, a coincidence degree calculation unit 202 for calculating coincidence degrees with respect to the automatic determination recipes, a coincidence degree estimation unit 203 for estimating a coincidence degree with respect to an image processing parameter set for which a coincidence degree is not calculated, on the basis of results given by the coincidence degree calculation unit 202, and a parameter determination unit 204 for determining an image processing parameter set to be automatically set, on the basis of a result given by the coincidence degree estimation unit 203.

Figure 3:
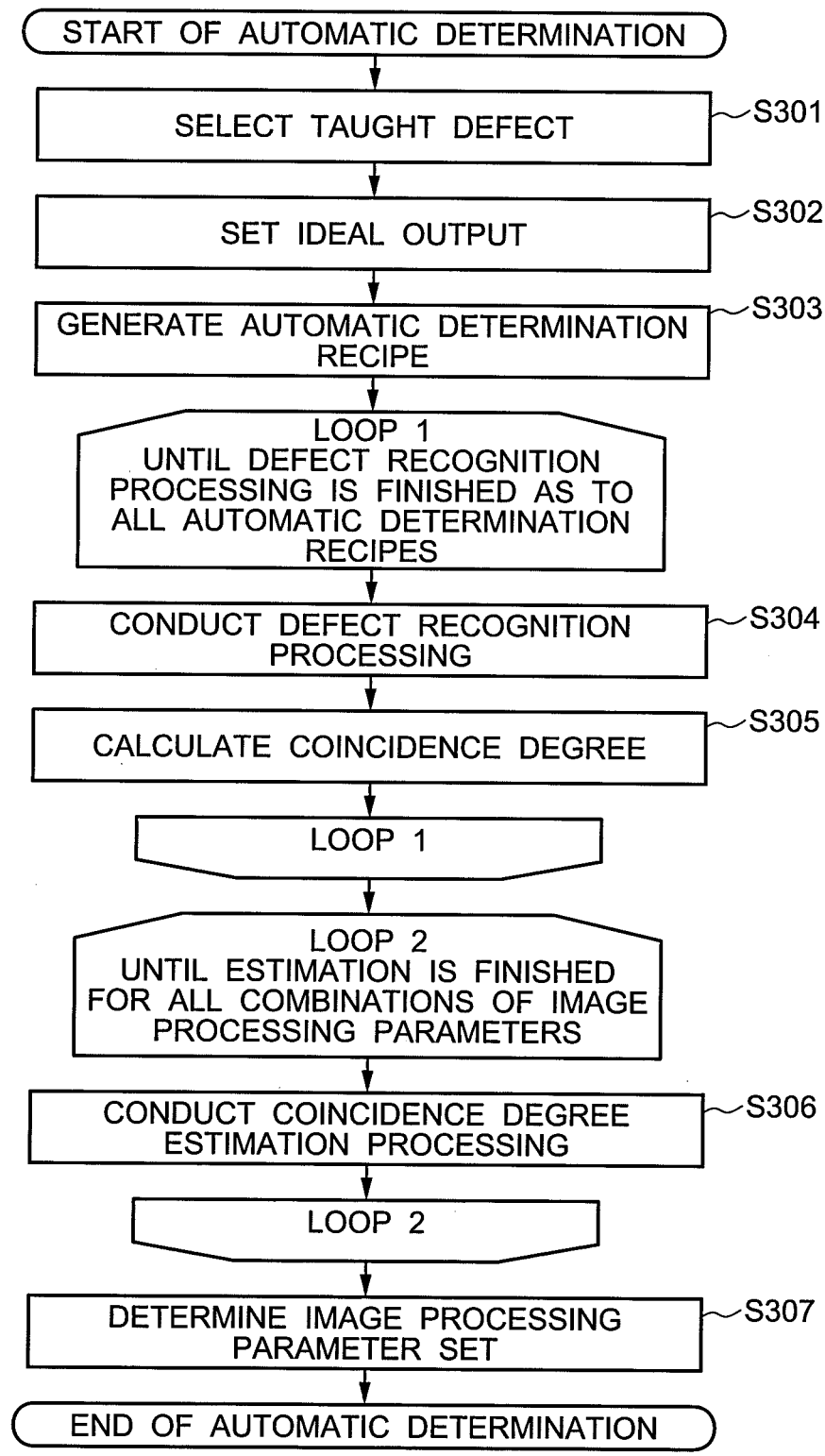
FIG. 3 is a flow chart showing processing in the automatic determination unit in the defect observation device according to the embodiment 1 of the present invention.

FIG. 3 is an example of a flow chart showing automatic adjustment processing of an image processing parameter set in the defect recognition processing.

Determination of an optimum image processing parameter set is conducted by conducting processing of each step in S301 to S307 shown in FIG. 3. Hereafter, details of processing and the data flow in FIG. 2 will be described along steps of S301 to S307 shown in FIG. 3.

1) At S301, a taught defect is selected on the basis of instruction information given by the user.

In the input/output unit 123 shown in FIG. 2, information of the taught defect selected by the user is input to a defect information storage unit 115. The defect information storage unit 115 inputs a defect image & non-defective article image of a taught defect to the defect recognition unit 119 on the basis of instruction information given by the user. In the present embodiment, three images in total composed of an image (an SE image) acquired from the secondary electron detector 110 and two images (an L image and an R image) acquired from the reflected electron detector 111 are input as each of the defect image and non-defective article image, with respect to the same one defect. By the way, the taught defect is not restricted to one defect, but a plurality of defects may be used.

1) At S302, an ideal output of defect recognition processing for a taught defect is set on the basis of instruction information given by the user.

An ideal output of a taught defect, for example, an ideal defect area is set by a user's input in the input/output unit 123 shown in FIG. 2. In this processing, for example, the user inputs an ideal state (ideal defect recognition result, i.e., an ideal output) obtained as a result of the defect recognition processing, while viewing a defect image displayed in the input/output unit. A concrete input procedure will be described later with reference to FIG. 4. By the way, information of the ideal output which is input is input to the coincidence degree calculation unit 202 for subsequent processing (S305). At this time, the number of ideal outputs which are input is not restricted to one with respect to one taught defect, but a plurality of ideal outputs may be input.

3) At S303, an automatic determination recipe is generated.

The automatic determination recipe generation unit 201 shown in FIG. 2 generates an automatic determination recipe on the basis of instruction information given by the user and accepted by the input/output unit 123, and inputs the automatic determination recipe to the defect recognition unit 119. In the present embodiment, the automatic determination recipe means a collection of a plurality of image processing parameter sets used in automatic determination processing (S304 to S307) of an image processing parameter set.

4) At S304, defect recognition processing is conducted on a taught defect under the condition of the automatic determination recipe.

The defect recognition unit 119 shown in FIG. 2 conducts defect recognition processing on the defect image/non-defective article image which is input from the defect information storage unit 115 by using the condition of the automatic determination recipe which is input from the automatic determination recipe generation unit 201, and inputs a recognition result (for example, defect areas processed under respective conditions) to the coincidence degree calculation unit 202.

3) At S305, a coincidence degree between the defect recognition result and the ideal output is calculated. By the way, at S304 and S305, the processing is continued until the coincidence degree is calculated as to all automatic determination recipes.

The coincidence degree calculation unit 202 shown in FIG. 2 compares the ideal output of the taught defect which is input from the input/output unit 123 (at S302) with the recognition result which is input from the defect recognition unit 119, and calculates a coincidence degree between them. The coincidence degree represents a similarity between the ideal output and the recognition result. For example, the coincidence degree is represented by a ratio between the number of overlapping pixels and the number of pixels in a defect area on the ideal output when images are superimposed.

By the way, if a plurality of ideal outputs are input with respect to one taught defect, it is also possible to compare a composite image of a plurality of ideal outputs which are input with a defect area of the recognition result and calculate a coincidence degree. As for the composite image, for example, an area (product area) recognized as a defect area in all recognition results and an area (sum area) recognized as a defect area in one or more recognition results when defect areas in a plurality of recognition results are superimposed can be considered. The coincidence degree is not restricted to the ratio in the number of pixels, but, for example, a feature quantity (such as, for example, a degree of circularity) in the ideal output or the composite image may be calculated and compared with the feature quantity in the recognition result.

In addition, a correspondence table (coincidence degree table) between the automatic determination recipe generated by the automatic determination recipe generation unit 201 and the coincidence degree is generated and input to the coincidence degree estimation unit 203. By the way, if there are a plurality of taught defects, an average of coincidence degrees of taught defects can be used as the coincidence degree.

6) At S306, estimation of the coincidence degree is conducted as to an image processing parameter set which is not included in the automatic determination recipe. In the estimation of the coincidence degree, a coincidence degree of a point other than sample points is estimated by using coincidence degrees of a small number of image processing parameter sets (sample points) for which coincidence degrees are calculated actually. For example, a multi-layer perceptron neural network which outputs coincidence degrees of points other than sample points by learning coincidence degrees of the sample points, or a design of experiments in which sample points are determined on the basis of an orthogonal array table and coincidence degrees of points other than the sample points are estimated by conducting an analysis of variance on coincidence degrees of the sample points may be used. The processing at S306 is continued until estimation is finished for all image processing parameter sets. In the example of S306, an example in which estimation is conducted for all image processing parameter sets is shown. Alternatively, however, estimation may be conducted for partial image processing parameter sets, such as, for example, image processing parameter sets having a high possibility that the coincidence degree will become high.

The coincidence degree estimation unit 203 shown in FIG. 2 estimates a coincidence degree as to an image processing parameter which is not included in the coincidence degree table, and inputs an estimation result of the coincidence degree to the parameter automatic determination unit 204.

7) At S307, an image processing parameter set having an estimated value of coincidence degree which has become high is determined as a setting candidate and displayed.

The parameter automatic determination unit 204 shown in FIG. 2 determines an image processing parameter set which becomes a setting candidate, out of the coincidence degree table which is input from the coincidence degree estimation unit 203, and outputs the image processing parameter set to the recipe storage unit 116. Furthermore, the determined parameter set is displayed in the input/output unit 123. GUI display contents in the input/output unit 123 will be described later with reference to FIG. 5. The image processing parameter set which is output is not restricted to one set, but a plurality of sets may be output.

The recipe storage unit 116 stores the determined image processing parameter set on the basis of the parameter determination result which is input from the parameter automatic determination unit 204. By the way, if a plurality of image processing parameter sets are determined as setting candidates, the user is made to select one image processing parameter set to be finally set.

According to the above-described procedure, even coincidence degree estimated values of a large number of image processing parameter sets can be calculated, compared and selected by using information of ideal outputs with respect to a small number of taught defects. As a result, it becomes possible to determine a suitable image processing parameter set. If a defect recognition result using the determined image processing parameter set is insufficient, then it is also possible to add or delete a taught defect by using a defect recognition result according to the determined image processing parameters and conduct the processing at S301 to S307 repetitively.

An example of an interface for inputting the ideal output information at S302 and an example of and an interface for displaying the defect recognition result using the image processing parameter set determined automatically at S307 will now be described with reference to FIG. 4 and FIG. 5, respectively.

Figure 4:
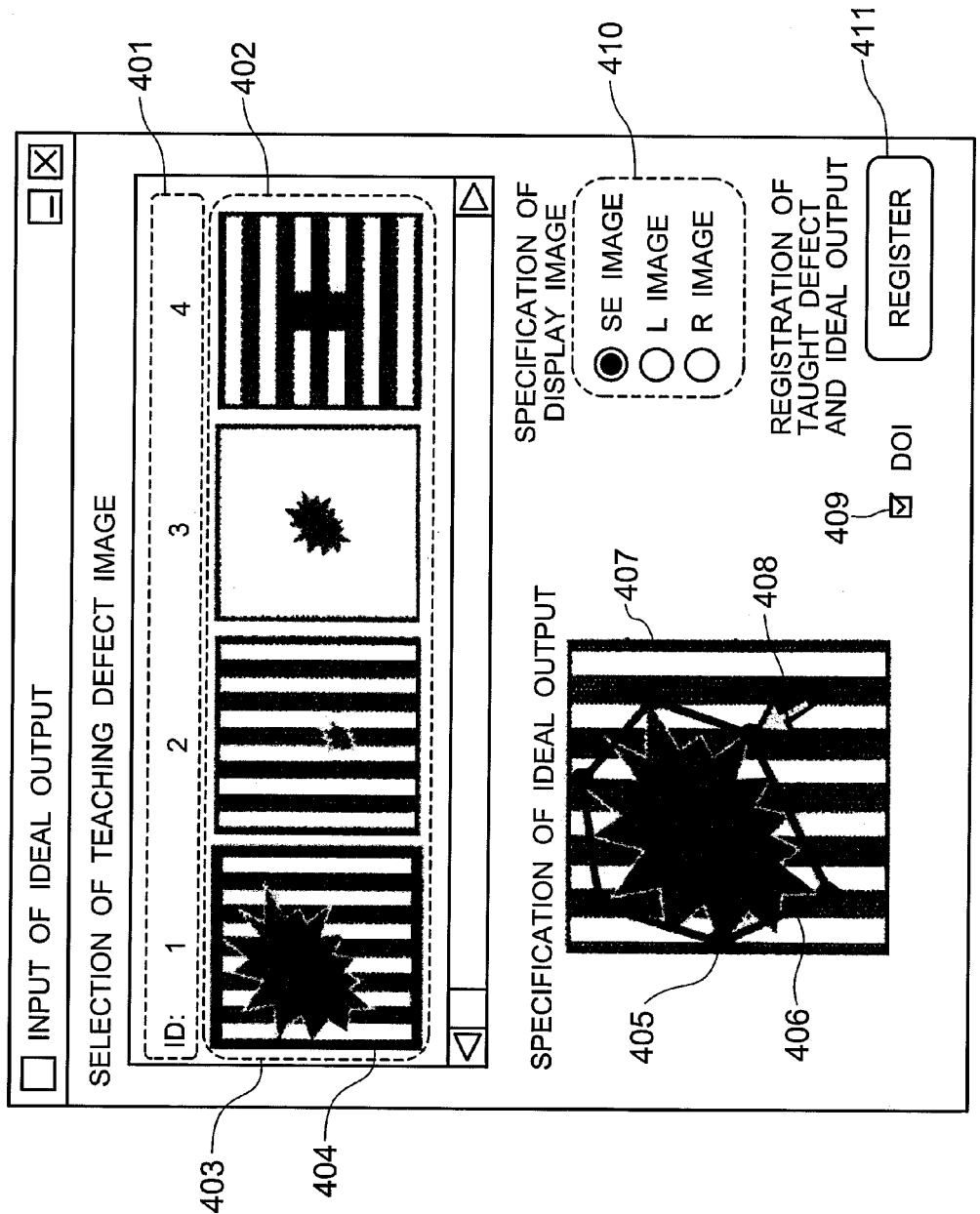
FIG. 4 is a diagram showing an example of an interface for selecting a taught defect and inputting an ideal output of defect recognition in the defect observation device according to the embodiment 1 of the present invention.

FIG. 4 shows an example of a GUI (Graphical User Interface) in the input/output unit 123 which accepts selection of taught defects and input of an ideal output of defect recognition in the defect observation device according to the embodiment 1 of the present invention. Hereafter, a method for selecting taught defects and inputting an ideal output will be described with reference to FIG. 4.

Reference numeral 401 denotes an identification number of a defect stored in the defect information storage unit 115, and reference numeral 402 denotes an image of a defect corresponding to the identification number. Reference numeral 403 denotes a defect contained in a defect image. At this time, an example in which images of four defects are displayed side by side. If the number of defects is large and the defects cannot be displayed in one screen, then displayed defects may be changed over by using a slide bar or the like or defects may be displayed in another GUI window or the like.

A taught defect is selected by means such as clicking an identification number 401 or a defect image 402 with a mouse.

Reference numeral 404 denotes a defect image selected as the taught defect.

Reference numeral 407 denotes an area where an ideal output in defect recognition processing of a defect selected by using the identification number 401 or the defect image 403 is input. In the present example, an image of a selected defect is displayed as a background image.

A defect image to be displayed as the background image of the input area 407 of the ideal output is selected by using 410. The present example is an example in which there are three defect images, i.e., an SE image, an L image, and an R image for one defect. As for the image displayed in the input area 407 of the ideal output, a mixed image of a plurality of images concerning the selected defect may be displayed, or a plurality of image may be displayed side by side.

By the way, taught defects may be selected automatically by using information of a defect kind which is previously input. Furthermore, it is also possible to narrow down candidates of a defect to be selected as taught defects by using information of the defect kind and display a result narrowed down on the GUI. An example of a GUI which accepts an instruction input for executing automatic selection of taught defects will be described later with reference to FIG. 10.

Positions in the input area 407 of ideal output are specified by means such as clicking with the mouse, and a closed area generated by coupling the specified positions is input as the ideal output.

Reference numeral 405 denotes a position specified by using means such as clicking with the mouse. Reference numeral 406 denotes a line formed by coupling specified positions. Reference numeral 408 denotes a pointer for specifying a position which is operated by using the mouse or the like.

By the way, a polygon generated by coupling specified positions with a straight line is input as the ideal output. Alternatively, however, an area formed by coupling specified positions with a curve may be input as the ideal output. The method for inputting the ideal output as well is not restricted to inputting by specifying positions one after another, but an image specifying an area of ideal output or data such as line segment data may be prepared previously and input. Or it is also possible to dispose various area drawing tools (such as a free hand tool for drawing a line with free hand, an eraser tool for deleting a drawn area, a range specification tool for specifying an area, a line drawing tool for drawing a straight line or a curve, and a paint out tool for painting out a specified area), draw a closed figure directly in the input area 407 of ideal output, and thereby input an ideal output.

After the selection of the taught defect and input of the ideal output, input information of the taught defect and ideal output is registered by using a registration button 411.

Reference numeral 409 denotes a check box for specifying whether the selected taught defect is a DOI. In the foregoing description, only information of the ideal output for the taught defect is input at S302 and the image processing parameter set is automatically determined in the processing at S302 to S307. If the defect kinds increases (for example, to 15 kinds or more), however, it becomes practically difficult to determine image processing parameter sets which yield favorable recognition results for any defect kind, in some cases. At that time, it is necessary to determine an image processing parameter set especially yielding favorable recognition results only about defects which are important to inspection and yield management. In such a case, it becomes useful to previously specify not only information of the ideal output but also a flag (DOI: Defect of Interest) indicating that the taught defect is important and automatically determine an image processing parameter set which especially makes the recognition result close to the ideal output as to the defect with the flag set. A region for specifying the DOI is the check box 409. By the way, determination of an image processing parameter set in the case where the DOI is set is conducted by setting a heavy weight if the taught weight is a DOI and a light weight otherwise when calculating a coincidence degree of a plurality of taught defects as the mean at S305, and thereby calculating the coincidence degree as the weighted mean As for concrete operation on the GUI, information as to whether the taught defect is a DOI is registered together by first checking the DOI setting check box 409 and then conduct registering with the registration button 411. The present example is an example in which the user is made to set whether a taught defect is DOI by using a GUI on which DOI setting can be set for taught defects. Alternatively, however, DOI information may be added automatically by previously giving information of defect kinds of taught defects.

Figure 10:
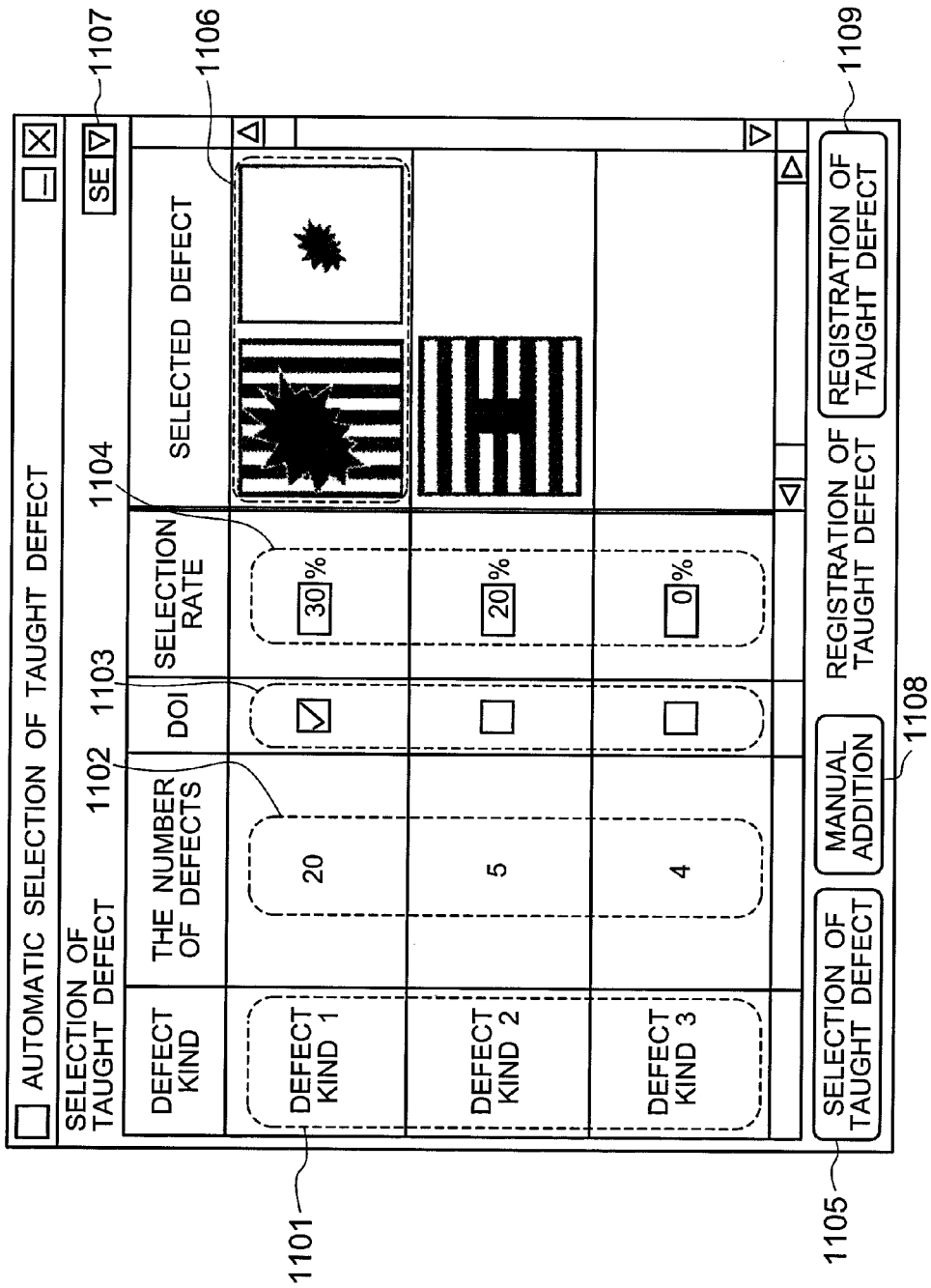
FIG. 10 is a diagram showing an example of an interface for inputting information concerning a defect in the defect observation devices according to the embodiments 1 to 3 of the present invention.

FIG. 10 shows an example of a GUI which accepts an input instruction for executing automatic selection of taught defects from the user, in the automatic determination recipe generation unit 201 in the defect observation device according to the embodiment 1 of the present invention. Taught defects are automatically selected from information concerning defects stored in the defect information storage unit 115, by using information of the defect kind and DOI information. Hereafter, an example of automatic selection of taught defects will be described with reference to FIG. 10.

Reference numeral 1101 denotes a list of defect kinds of defects stored in the defect information storage unit 115, and 1102 denotes the number of defects belonging to each defect kind. Here, display of the defect kind list 1101 is not restricted to the example shown in FIG. 10, but representative images of respective defect kinds may be displayed. Or the defect kind may be displayed by using a term indicating a kind of a defect kind or a feature of a shape, such as a foreign material or scratch. In 1102, an example displaying the number of defects is displayed is shown. Alternatively, however, a value such as a feature quantity which becomes a reference of taught defect automatic selection may be displayed as an index. Reference numeral 1103 denotes a check box for specifying whether the corresponding defect kind is a DOI.

Reference numeral 1104 denotes a text box for specifying information representing a percentage of defects to be selected from defect kinds, with respect to the number of defects or another index displayed in 1102. The present example is an example in which specification is conducted every defect kind. Alternatively, however, a GUI which specifies the same value for all defect kinds may be provided. Instead of proportions of selection of taught defects, an item for inputting the number of taught defects to be selected may be provided to allow for the user to directly input the number of taught defects to be selected. Furthermore, in FIG. 10, an example in which the proportions of the taught defects are specified by 1104 is shown. Instead of causing the user to specify proportions or numbers in selection, however, a method of automatically setting them on the basis of information of 1103 or the like is conceivable. A setting method such as selecting more defects from a defect kind for which DOI information is set than a defect kind for which DOI information is not set, on the basis of 1103 is conceivable.

Figure 11:
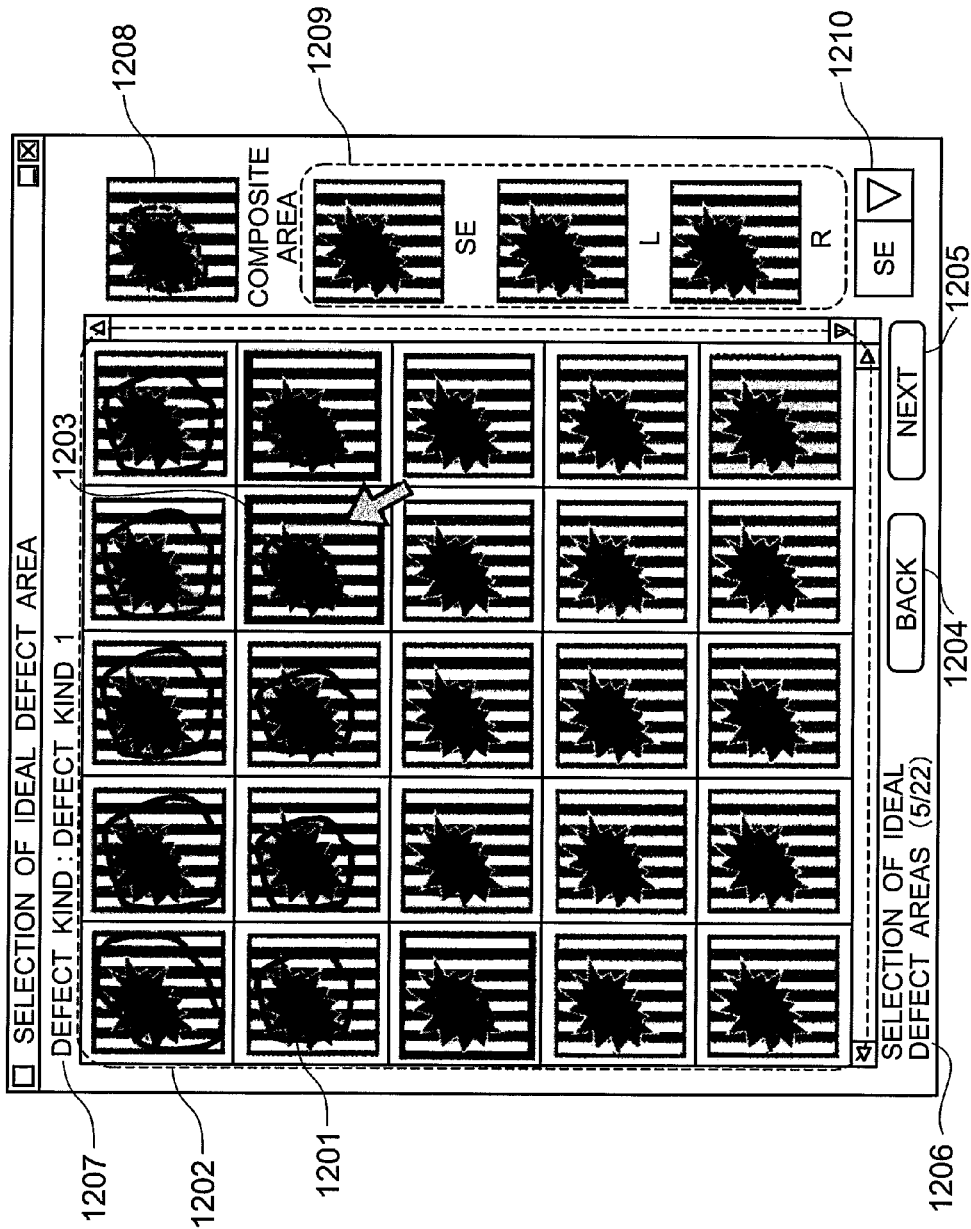
FIG. 11 is a diagram showing an example of an interface for selecting a taught defect and inputting an ideal output of defect recognition in a defect observation device according to an embodiment 3 of the present invention.

Reference numeral 1105 denotes a button for executing automatic selection of a defect on the basis of information of 1101 and 1102 and setting of 1103 and 1104. As for a method for automatic selection of taught defects, a method of extracting as many taught defects as a proportion specified by 1104 every defect kind randomly, a method of preferentially extracting taught defects selected as taught defects in the past, or the like is conceivable. In an example of a defect kind 1 shown in FIG. 10, the number of defects is 20 and the selection ratio is 30%. As a result, six defects are extracted randomly and selected as taught defects. By the way, if it is impossible to display all of the six defects on one screen as shown in FIG. 11, a slide bar or the like should be used.

Reference numeral 1106 denotes a display part of an automatically selected defect. Here, an example in which defects are divided into corresponding defect kinds and displayed is shown. A displayed image (such as an SE image, an L image, and an R image) can be changed by using a combo box 1107. Furthermore, an image obtained by mixing two or more images may be displayed in the display part 1106. If in this case there are a plurality of images extracted randomly, setting may be conducted previously to compose them automatically. Or after a plurality of images are extracted, a plurality of images selected by the user may be composed out of them. If a selection result displayed in the display part 1106 is insufficient, manual addition of defects using a button 1108 is also possible. Reference numeral 1109 denotes a button for registering a defect displayed in 1106 as a taught defect.

The example in which a taught defect is automatically selected by using information of a defect kind as reference has been described with reference to FIG. 10. However, information used as the reference is not restricted to the defect kind. For example, if interconnection recognition is an object, then a feature quantity such as roughness and fineness of a circuit pattern in a non-defective article image may be used as the reference and various indexes serving as the reference can be selected.

Figure 5:
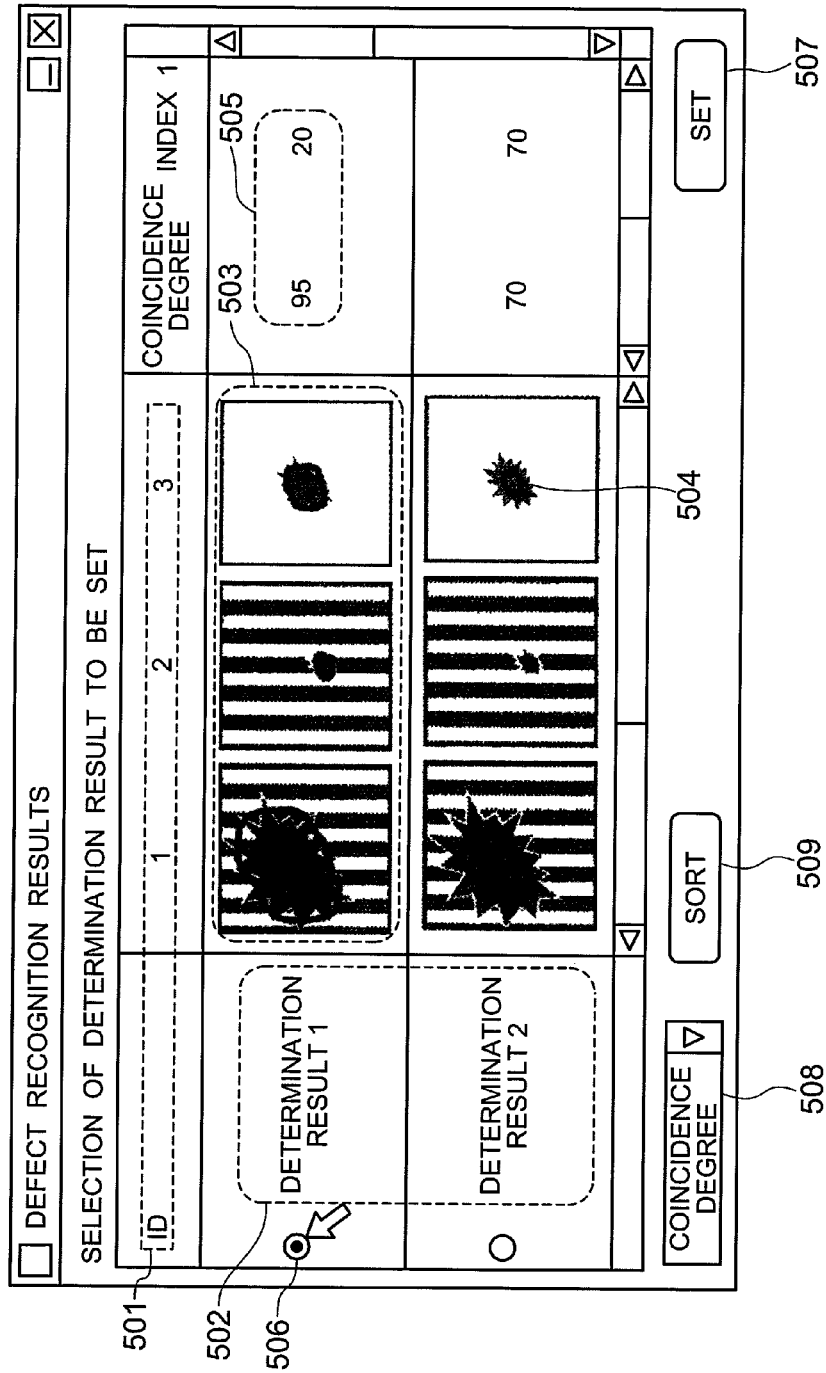
FIG. 5 is a diagram showing an example of an interface for displaying a defect recognition result for an image processing parameter set determined by the automatic determination unit in the defect observation device according to the embodiment 1 of the present invention.

FIG. 5 shows an example of a GUI which displays a defect recognition result based upon an automatic determination result (which means, in the embodiment 1, a determined image processing parameter set) of the automatic determination unit in the defect observation device according to the embodiment 1 of the present invention, and specifies an image processing parameter set. FIG. 5 shows an example in which a plurality of automatic determination results are output and defect recognition results of three taught defects based upon two determination results are displayed.

Reference numeral 501 denotes an identification number of a taught defect, 502 denotes display of an identification name of a determination result, and 503 denotes an example in which defect recognition results in a first determination result which is automatically determined are displayed side by side.

Reference numeral 504 denotes an area subjected to defect recognition. In the present example, the area is displayed by a closed line to be superimposed on an image of a taught defect. Alternatively, however, the defect recognition result may be displayed side by side with the image of the taught defect, or may be displayed in a different GUI window. The ideal output may also be displayed to be superimposed on the image of the taught defect, displayed side by side with the image of the taught defect, or may be displayed in a different GUI window, together with the defect recognition result. By the way, the area subjected to defect recognition and the ideal output may be displayed with a changed color, line thickness, line kind, or the like, or may be displayed by painting out the area with a color different from a background color or a semitransparent color having a color different from the background color.

Reference numeral 505 denotes an estimated value of the coincidence degree in the first determination result and an index value which can be utilized by the user to select a determination result to be finally set. It is also possible to actually conduct defect recognition processing on the basis of the selected determination result and display a calculated coincidence degree. The present example is an example in which only an index value of one kind is displayed in addition to an estimated value of the coincidence degree. Alternatively, however, a plurality of index values may be displayed.

Reference numeral 506 denotes a radio button for selecting a determination result to be finally set. After the selection, a determination result is determined by using a setting button 507.

By the way, if the defect recognition result, the determination result, and the index value cannot be displayed in one screen, the displayed defect may be changed over by using a slide bar or the like, or they may be displayed in a different GUI window.

Reference numeral 508 denotes a list box which makes it possible to select a reference for rearranging display of the defect recognition result, and the coincidence degree, the index value, or the like is selected.

Reference numeral 509 denotes a button for rearranging displayed determination results in the order of height with respect to the reference in 508. By the way, it is also possible to set a threshold previously and display only defect recognition results which are at least the threshold in calculated coincidence degree or index. It is also possible to conduct setting to automatically select a defect recognition result which is maximum in coincidence degree or index value.

The coincidence degree table will now be described with reference to FIG. 6.

The coincidence degree table is a table which stores coincidence degrees with respect to automatic determination recipes, and the coincidence degree table is generated in the coincidence degree calculation unit 202 shown in FIG. 2.

Figure 6:
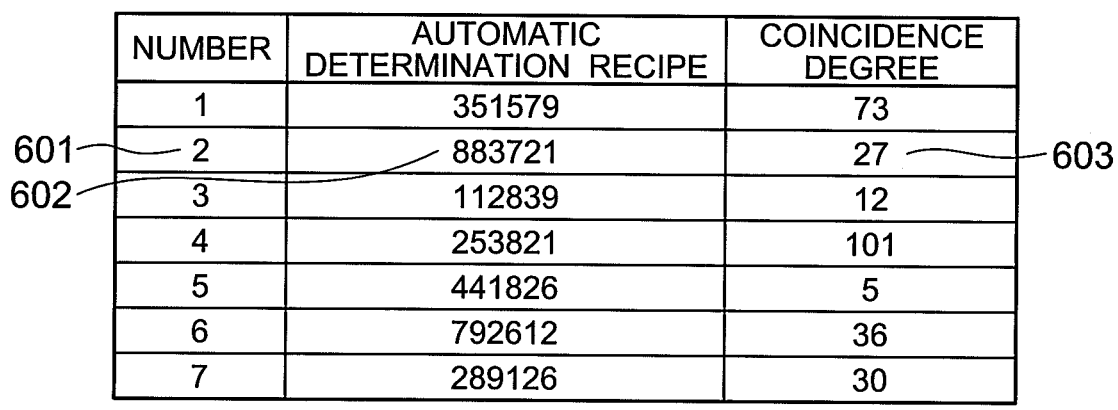
FIG. 6 is a diagram showing an example of a coincidence degree table generated by a coincidence degree calculation unit in the defect observation device according to the embodiment 1 of the present invention.

FIG. 6 shows an example of the coincidence degree table in the case where the number of the automatic determination recipes is seven sets, the number of parameters included in the image processing parameter set to be set is six, and a value which can be set in each parameter is in the range of 1 to 9.

In FIG. 6, reference numeral 601 denotes a number of an automatic determination recipe, and 602 denotes a first automatic determination recipe (which means, in the embodiment 1, an image processing parameter set). In the present example, setting values of respective image processing parameters are arranged in order and displayed as inscription of the image processing parameter set. In the example of 602, a setting value of a first image processing parameter is 3 and a setting value of a second image processing parameter is 5.

Reference numeral 603 denotes a coincidence degree calculated in the first automatic determination recipe. By the way, if there are a plurality of taught defects, then coincidence degrees of respective taught defects may be stored, or one coincidence degree may be stored by combining the coincidence degrees of respective calculated taught defects. Furthermore, in the present example, only coincidence degrees are stored in the coincidence degree table. However, the stored index values are not restricted to coincidence degrees, but an index value which can be utilized to determine the image processing parameter set and information as to whether the taught defect is a DOI may be stored together.

In the first embodiment of the present invention, an example of automatic determination of the image processing parameters in the defect recognition unit 119 has been described. However, this is nothing but an example. Within the scope of the same spirit, various variations may be used, for example as described hereafter.

a) Device for Automatically Determining Image Processing Parameter Set

In the foregoing description, the embodiment of the present invention has been described by taking processing for the defect recognition unit 119 as an example. However, the embodiment of the present invention is not restricted to this, but it can be also applied to the interconnection recognition unit 120 or other devices having a plurality of image processing parameters used in image processing, in the same way.

b) The Number of Defect Images and Non-Defective Article Images which are Input

It has been described that three defect images and three non-defective article images are input to the defect recognition unit 110 with respect to one taught defect at S301. In the present example, a defect observation device having three detectors is taken as an example, and consequently three images are input as described above. However, the present invention is not restricted to this, but an arbitrary number of images can be input depending upon the number of detectors.

c) Automatic Deter Urination Recipe

It has been supposed that the generated automatic determination recipe is generated in the automatic determination recipe generation unit 201 at S303. However, the automatic determination recipe is not restricted to automatic generation, but the automatic determination recipe may be set arbitrarily by the user or may be defined previously.

d) Image Processing Parameter Set Determination Technique

When determining an image processing parameter set at S307, a technique of narrowing down candidates of the image processing parameter set which are output on the basis of estimation processing and determination processing of a plurality of stages may be used. For example, a technique of determining a plurality of image processing parameter sets having a high estimated value of coincidence degree as a first stage of the image processing parameter set determination, regenerating an automatic determination recipe by using a plurality of image processing parameter sets determined in the first stage as a second stage, and repeating the coincidence degree calculation processing and coincidence degree estimation processing is also conceivable.

Furthermore, the method for determining an image processing parameter set by using the estimated value of the coincidence degree as the reference is not restrictive. It is also possible to actually conduct defect recognition processing in the defect recognition unit 119 and determine the image processing parameter set of a setting candidate by using a result of calculating a coincidence degree with the ideal output in the coincidence degree calculation unit 202.

For example, a method of conducting defect recognition processing and coincidence degree calculation on one image processing parameter set or a plurality of image processing parameter sets in order from an image processing parameter set having a high coincidence degree and determining an image processing parameter set having a high coincidence degree out of image processing parameter sets subjected to coincidence degree calculation as a setting candidate is conceivable.

In addition, in the determination processing of the image processing parameter set, it is also possible to prepare a plurality of processing modes which differ in parameter search range, cause the user to select a mode previously, and conduct processing of the mode. In this case, in a mode having a sufficiently wide search range, the possibility that a parameter set having a high coincidence degree will be able to be determined is high, but there is a possibility that the search time will increase. On the other hand, in a mode having a narrow search range, only a parameter set having a low coincidence degree might be obtained, but it becomes possible to determine a parameter set fast. The user selects one out of a plurality of processing modes from a viewpoint of precision and processing time, and executes it. By the way, the user may specify a mode interactively by using a GUI. Or it is also possible to previously prepare data which describes a relation between parameter determination processing and a processing mode at that time, in a format of a batch file and execute parameter determination processing a plurality of times on the basis of contents of the data.

As described heretofore, in the present embodiment, sensible setting becomes possible for setting of an image processing parameter set by causing the input information to be the ideal output. It becomes possible to save the user the trouble of trial and error by automatically determining an image processing parameter set after input of the information. It becomes possible to make the processing speed fast as compared with the case where image processing is conducted for all image processing parameter sets by conducting image processing on only a small number of limited image processing parameter sets and estimating results of all image processing parameter sets. As a result, it becomes possible to set an image processing parameter set required to classify the defect kind easily and fast.

Embodiment 2

Embodiment 2 is obtained from the embodiment 1 by automatically determining not only an image processing parameter set but also an image processing algorithm in the case where the defect recognition unit 119 and the interconnection recognition unit 120 have a plurality of image processing algorithms. A configuration of a defect observation device such as the SEM image acquisition unit 130 other than the automatic determination unit and processing other than the automatic determination processing are similar to those in the embodiment 1. Accordingly, only different points will now be described mainly. In the embodiment 2, the image processing parameter set included in the automatic determination recipe, the coincidence degree table, the coincidence degree estimation result, and the determination result of the automatic determination in the embodiment 1 becomes a combination of an image processing algorithm and an image processing parameter set.

A feature quantity calculation conducted in the interconnection recognition unit 120 in the defect observation device according to the embodiment 2 of the present invention, in the case where a plurality of image processing algorithms are included will now be described with reference to FIG. 7.

Figure 7:
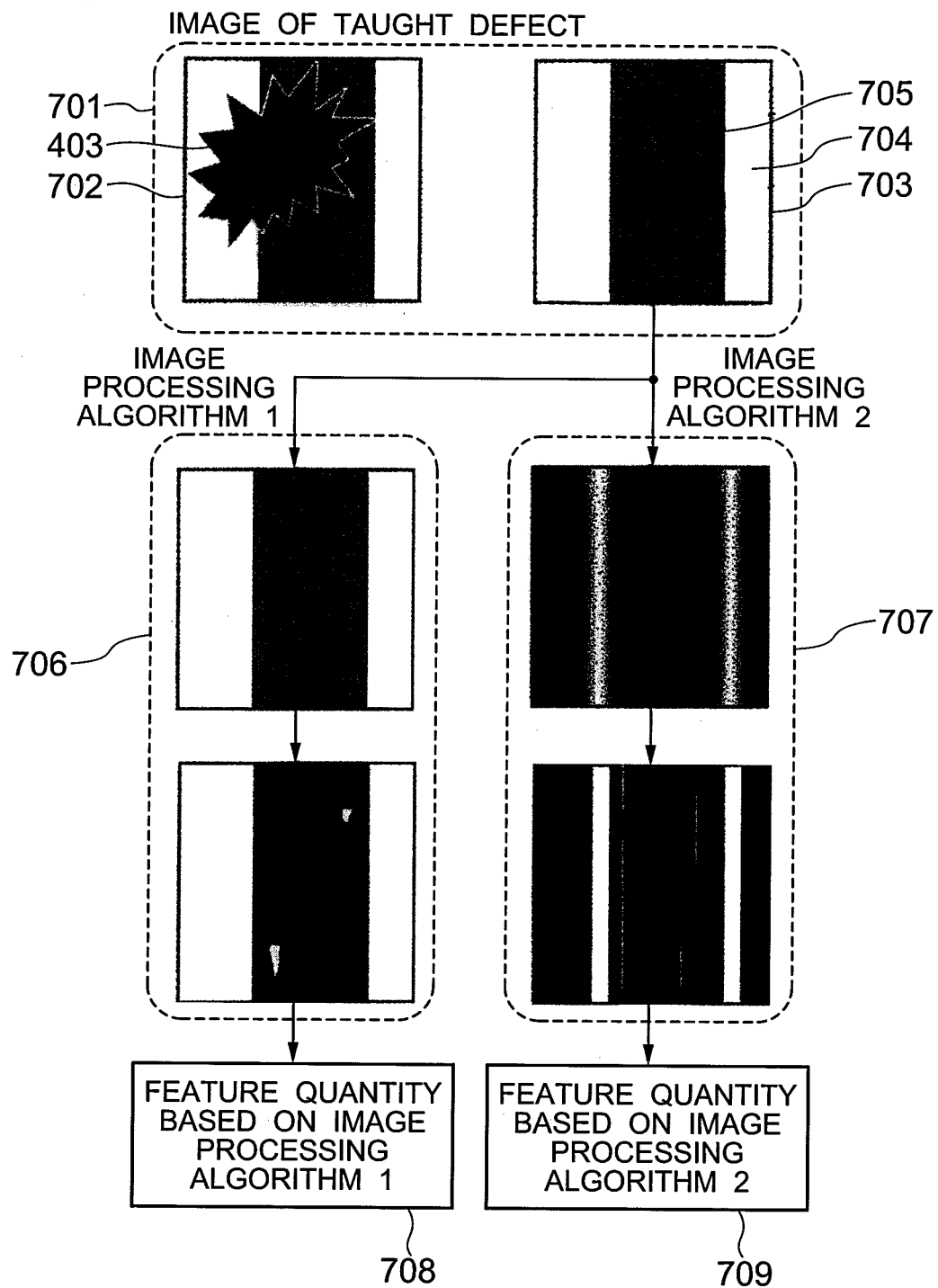
FIG. 7 is a diagram showing an example of feature quantity calculation processing in the case where an interconnection recognition unit in a defect observation device according to an embodiment 2 of the present invention has a plurality of image processing algorithms.

FIG. 7 is a diagram showing a flow of feature quantity calculation based on processing of a plurality of image processing algorithms in the interconnection recognition unit 120 in the defect observation device according to the embodiment 2 of the present invention. The present example shows an example in which the feature quantity is calculated according to an algorithm 1 for conducting interconnection recognition by using a luminance value as reference and an algorithm 2 for recognizing an interconnection on the basis of edge information of the interconnection.

In FIG. 7, reference numeral 701 denotes an image (interconnection image for teaching) of a taught defect which is input to the interconnection recognition unit 120, 702 denotes a defect image, and 703 denotes a non-defective article image. Furthermore, reference numeral 704 denotes an interconnection part, and 705 denotes an underlying interconnection.

Reference numeral 706 denotes an intermediate result of image processing according to an image processing algorithm 1, and 707 denotes an intermediate result of image processing according to an image processing algorithm 2. For generating intermediate results, it is necessary to set parameters which differ according to utilized image processing algorithm, such as a luminance threshold value for recognizing an interconnection in the case of the image processing algorithm 1 and a size of an image processing filter for conducting edge detection in the case of the image processing algorithm 2. Furthermore, the image processing algorithms 1 and 2 may have a common parameter such as a mixture ratio. Here, an example using two image processing algorithms has been shown. However, this is not restrictive, but another image processing algorithm for interconnection processing may be used, or three or more image processing algorithms may be used.

Reference numeral 708 denotes a feature quantity calculated by using the image processing algorithm 1, and 709 denotes a feature quantity calculated by using the image processing algorithm 2. As for the feature quantity calculated by the interconnection recognition unit 120, a result which differs depending upon the utilized image processing algorithm and image processing parameter set is output.

A method for determining an image processing algorithm and an image processing parameter set in the automatic determination unit in the defect observation device according to the embodiment 2 of the present invention will now be described with reference to FIG. 8.

Figure 8:
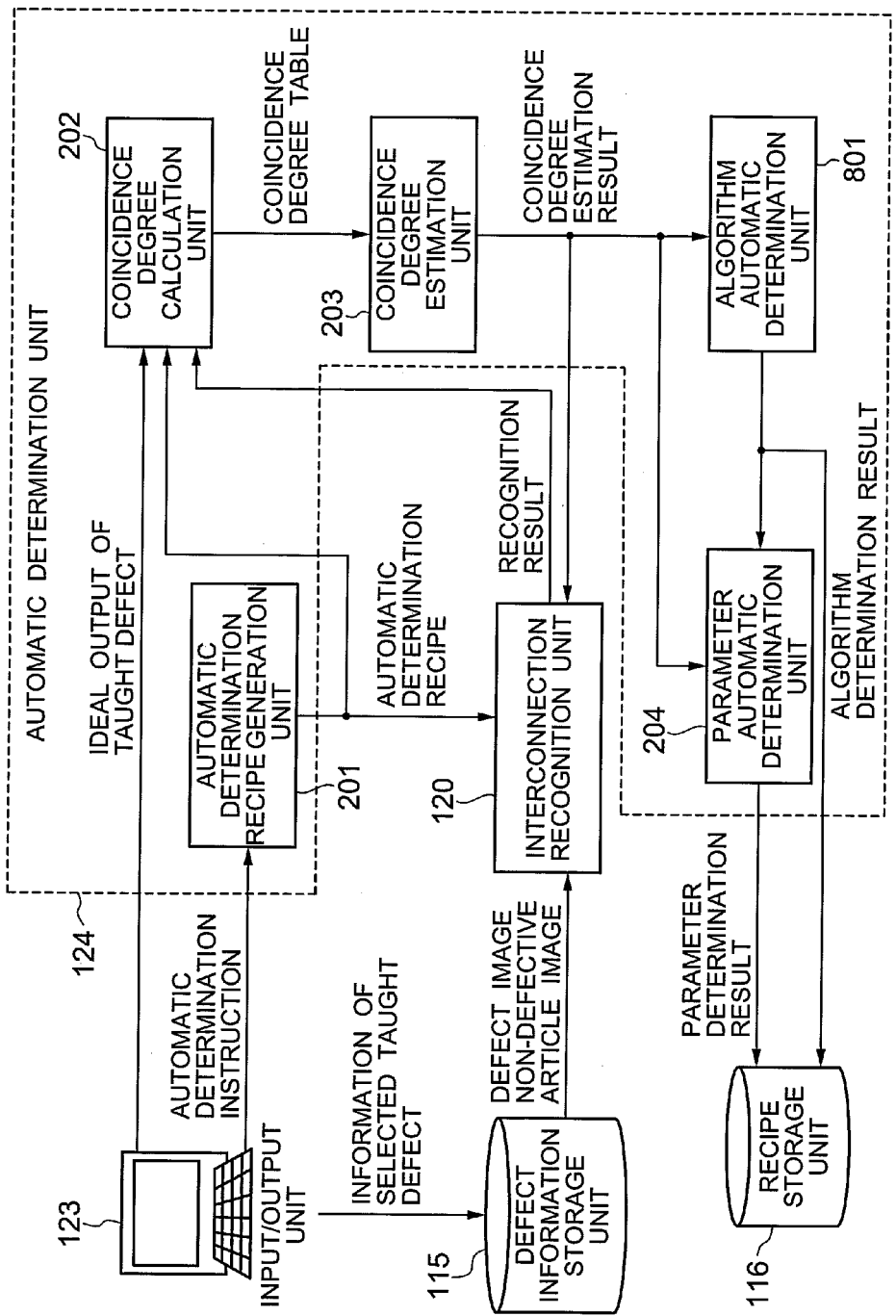
FIG. 8 is a diagram showing a device configuration and a data flow in an automatic determination unit in the defect observation device according to the embodiment 2 of the present invention.

FIG. 8 is a diagram showing a device configuration and a data flow in the automatic determination unit 124 in the defect observation device according to the embodiment 2 of the present invention.

In the embodiment 1, the coincidence degree calculation unit 202 finds a coincidence degree between the ideal output (a defect area in an image) of a taught defect and an image processing result calculated by using the automatic determination recipe, the coincidence degree estimation unit 203 conducts coincidence degree estimation on the basis of a result of the finding and then inputs a result of the coincidence degree estimation to the parameter automatic determination unit 204, and the parameter automatic determination unit 204 conducts determination of an image processing parameter set.

In the embodiment 2, the object is interconnection recognition. Accordingly, the ideal output of a taught defect is not a defect area, but becomes an area of an interconnection of the recognition object. Specifically, information of an area (interconnection area 704) where an image of an interconnection is taken in an image becomes an ideal output as an ideal interconnection area. In addition, the present embodiment differs from the embodiment 1 in that an algorithm automatic determination unit 801 for determining an image processing algorithm is added to the automatic determination unit 124.

The coincidence degree calculation unit 202 conducts coincidence degree calculation for all automatic determination recipes (which are, in the embodiment 2, combinations of image processing algorithms and image processing parameter sets), generates a coincidence degree table, and inputs the coincidence degree table to the coincidence degree estimation unit 127.

The coincidence degree estimation unit 203 conducts coincidence degree estimation for all combinations of image processing algorithms and image processing parameter sets, and inputs coincidence degree estimation results to the algorithm automatic determination unit 801 and the parameter automatic determination unit 204.

The algorithm automatic determination unit 801 determines an image processing algorithm, and the parameter automatic determination unit 204 determines an image processing parameter set in the determined image processing algorithm on the basis of the coincidence degree estimation results.

After the determination, a defect recognition result according to a determination result (which means, in the embodiment 2, a combination of an image processing algorithm and an image processing parameter set) determined by the automatic determination unit 124 is displayed.

In the embodiment 2, an example of automatic determination of an image processing algorithm and an image processing parameter set in the interconnection recognition unit 120 has been described. However, the present invention is not restricted to the defect recognition unit 119 or the interconnection recognition unit 120, but the present invention can be also applied to other devices in which an operation result can be used in feature quantity calculation and which have a plurality of image processing algorithms and image processing parameters. Even if the image processing algorithm in those devices has a different number of image processing parameters of different kinds, the present invention can be applied to those devices.

In the present embodiment, therefore, it becomes possible to set image processing algorithms and image processing parameter sets easily and fast with respect to a device in which an operation result can be used in feature quantity calculation and which have a plurality of image processing algorithms and image processing parameters, as well.

Embodiment 3

Embodiment 3 is obtained from the embodiment 1 by changing the taught defect selection method and the ideal output inputting method. A configuration and processing of a defect observation device is the same as those in the embodiment 1, and they will be omitted in description. Furthermore, the present invention is not restricted to the case where the image processing parameter set is automatically determined as in the embodiment 1, but the present invention can also be applied to the case where the image processing algorithm and the image processing parameter set are automatically determined as in the embodiment 2.

Figure 9:
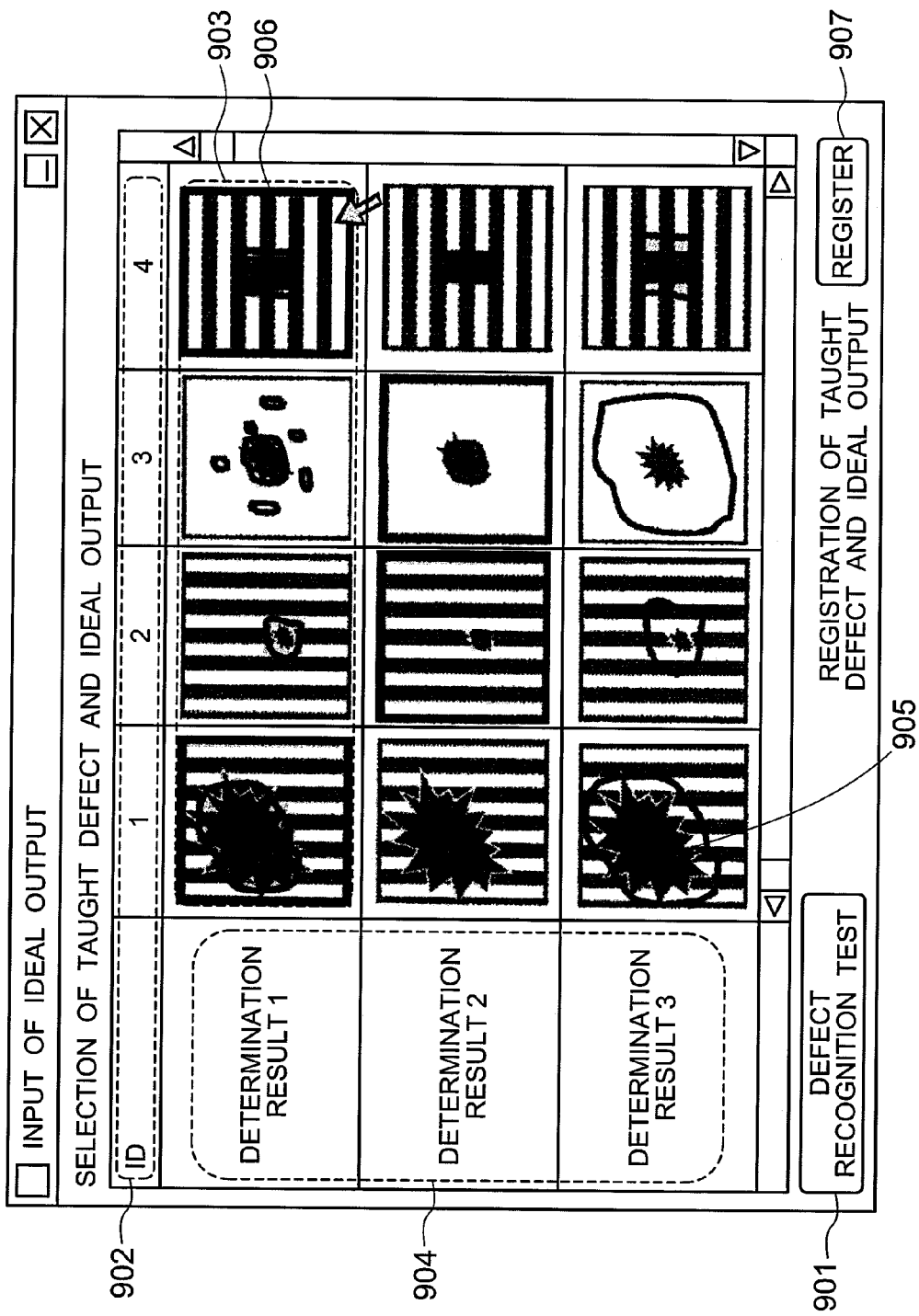
FIG. 9 is a diagram showing an example of an interface for selecting a taught defect and inputting an ideal output of defect recognition in a defect observation device according to an embodiment 3 of the present invention.

Hereafter, the taught defect selection method and the ideal output inputting method in the automatic determination unit in the defect observation device according to the embodiment 3 of the present invention will be described with reference to FIG. 9. FIG. 9 is a diagram showing an example of a GUI for selecting a taught defect and inputting an ideal output of defect recognition according to embodiment 3 of the present invention.

In the embodiments 1 and 2, a defect to be used as a taught defect is selected out of defect images arranged side by side as shown in FIG. 4, positions are specified by means such as clicking an area of an ideal output of defect recognition with a mouse, and a closed area generated by coupling the specified positions is input as an ideal output. In the present embodiment, an ideal output is input by selecting a defect recognition result every taught defect from a list of defect recognition results according to several image processing parameter sets as shown in FIG. 9. By the way, in an example shown in FIG. 9, a list of defect recognition results is displayed for three image processing parameter sets and four defects. If the list cannot be displayed in one screen, however, displayed defects may be changed over by using a slide bar or the like or the defects may be displayed in a different GUI window or the like.

In FIG. 9, reference numeral 901 denotes a button for selecting a prescribed number of image processing parameter sets randomly, conducting defect recognition processing on respective image processing parameter sets of defects images, and displaying a list of defect recognition results. The prescribed number may be prepared, or may be specified arbitrarily by the user. By the way, when automatically determining a combination of an image processing algorithm and an image processing parameter set as in the embodiment 2, combinations of image processing algorithms and image processing parameter sets are selected randomly, and a list of results obtained by conducting defect recognition processing with respect to respective combinations is displayed. Furthermore, in the present invention, image processing parameter sets used in list display are not restricted to random selection, but they may be selected by using a table of image processing parameter sets prepared previously or may be selected arbitrarily by the user.

As for the image processing parameter sets used in the list display, image processing parameter sets defined in an orthogonal array table which is utilized when using a design of experiments in the coincidence degree estimation unit may be used. An example using image processing parameter sets defined in an orthogonal array table will be described later with reference to FIGS. 11 and 12.

In the present example, a list of results obtained by conducting defect recognition processing on the same image processing parameter set with respect to all defects is displayed. Alternatively, however, a list of results obtained by conducting defect recognition processing on a parameter set which differs from defect to defect may be displayed.

Reference numeral 902 denotes an identification number of a defect. Reference numeral 903 denotes defect recognition results of defects corresponding to a first selected image processing parameter set. Reference numeral 904 denotes identification numbers of selected image processing parameter sets.

Reference numeral 905 denotes an area of a defect recognition result. In the present example, the area is displayed by a line to be superimposed on a defect image. As for 905, the defect recognition result may be displayed side by side with the image of the defect, or may be displayed in a different GUI window, in the same way as 504 in FIG. 5. The ideal output may also be displayed to be superimposed on the image of the defect, displayed side by side with the image of the defect, or may be displayed in a different GUI window, together with the defect recognition result. By the way, the area subjected to defect recognition and the ideal output may be displayed with a changed color, line thickness, line kind, or the like, or may be displayed by painting out the area with a color different from a background color or a semitransparent color having a color different from the background color.

Reference numeral 906 denotes a selected taught defect and a defect recognition result used as an ideal output. One defect recognition result used as an ideal output or a plurality of defect recognition results used as ideal outputs are selected for each defect from the defect recognition result in 905. By the way, an ideal output may be selected for each of all defects, or may be selected for each of only defects having a possibility of being used as a taught defect.

Reference numeral 907 denotes a button for registering the selected defect and defect recognition result as a taught defect and an ideal output. The taught defect and the ideal output can be registered by selecting the taught defect and the defect recognition result to be used as the ideal output and then pressing the button.

Figure 12:
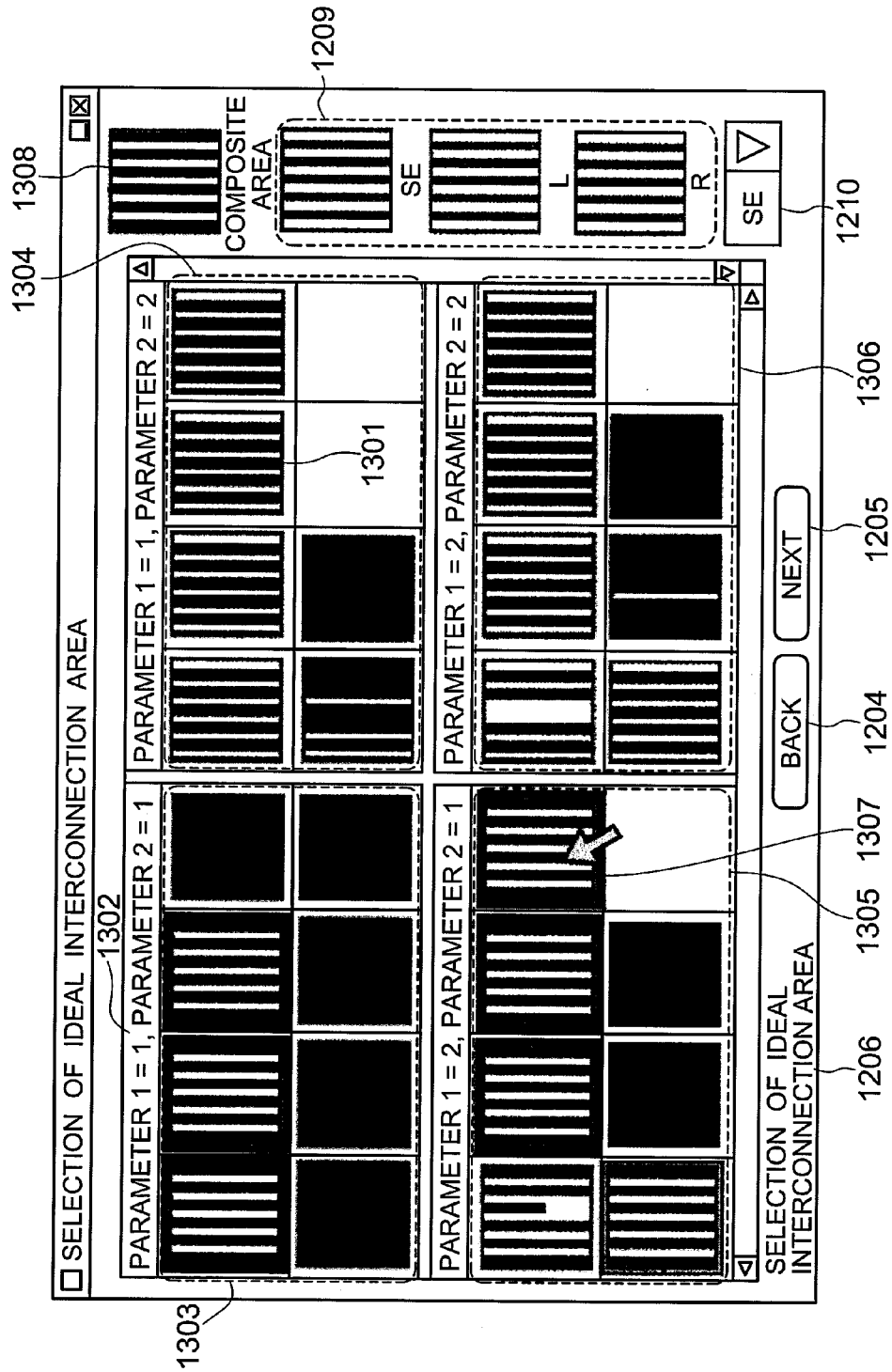
FIG. 12 is a diagram showing an example of an interface for selecting a taught defect and inputting an ideal output of defect recognition in a defect observation device according to an embodiment 3 of the present invention.

Furthermore, in the taught defect selection method and ideal out inputting method in the automatic determination unit 124 in the defect observation device according to the embodiment 3, it is also possible to apply a GUI as shown in FIG. 11 and FIG. 12 instead of the GUI shown in FIG. 9. Hereafter, the taught defect selection method and ideal out inputting method in the automatic determination unit in the defect observation device according to the embodiment 3 of the present invention will be described with reference to FIGS. 11 and 12.

FIG. 11 is a diagram showing an example of a GUI for selecting a taught defect and inputting an ideal output of defect recognition according to the embodiment 3 of the present invention. FIG. 12 is a diagram showing an example of a GUI for selecting a taught defect and inputting an ideal output of interconnection recognition according to the embodiment 3 of the present invention. By the way, FIG. 11 and FIG. 12 show examples in which image processing results in one taught defect are displayed with respect to one GUI window. The user inputs an ideal output for one taught defect, changes over a GUI window, and inputs an ideal output for another taught defect.

In FIG. 11, reference numeral 1201 denotes an area of defect recognition result. In the present example, the area is displayed by a line to be superimposed on a defect image. By the way, the area 1201 may be displayed side by side with a defect image, or may be displayed in a different GUI window. Furthermore, the ideal output may also be displayed to be superimposed on the image of the defect, displayed side by side with the image of the defect, or may be displayed in a different GUI window, together with the defect recognition result. By the way, the area subjected to defect recognition and the ideal output may be displayed with a changed color, line thickness, line kind, or the like, or may be displayed by painting out the area with a color different from a background color or a semitransparent color having a color different from the background color.

Reference numeral 1202 denotes a list of defect recognition results in an image processing parameter set defined in an orthogonal array table, and the defect recognition results are displayed in order of decreasing size of recognized defect area. As for the defect recognition results displayed in 1202, defect recognition results may be displayed with respect to all image processing parameter sets defined in the orthogonal array table, or may be displayed with respect to only a part of them. The image processing results displayed in 1202 are not restricted to image processing results in the image processing parameter set described in the orthogonal array table, but the image processing results displayed in 1202 may be image processing results in the image processing parameter set defined by the user previously, or the image processing results displayed in 1202 may be image processing results in the image processing parameter set which is set randomly. Furthermore, the list of defect recognition results in 1202 is not restricted to the size order of the recognized area, but the list may be displayed in the order of image processing parameter value in the image processing parameter set or the list may be displayed in the order of the value of the feature quantity (such as the degree of circularity) of defect recognition result. The user can select one of these kinds of rearrangement by using a rearrangement button (not illustrated) for executing rearrangement under a predetermined condition.

Reference numeral 1203 denotes a defect recognition result used as the selected ideal output. In the example shown in FIG. 11, selected defect recognition results are displayed emphatically with thick frames for the user to be able to discriminate them. One or a plurality of defect recognition results used as the ideal output are selected from the list 1202 of defect recognition results, for each display defect. By the way, it is also possible not to select even one ideal processing result. Processing such as excluding defects having image processing results displayed in the window from taught defects (i.e., keeping from coincidence degree calculation) may be conducted by selecting nothing at all.

Reference numerals 1204 and 1205 denote buttons for changing displayed image processing results to image processing results of another taught defect. A number of a taught defect which is being displayed at the present time and the number of all taught defects are indicated in 1206. In the example shown in FIG. 11, image processing results are being displayed for a fifth taught defect out of twenty-two taught defects. Image processing results of a fourth taught defect are displayed by pressing the button 1204, and image processing results of a sixth taught defect are displayed by pressing the button 1205. An ideal output is input with respect to a taught defect for which image processing results are being displayed. By the way, as for the order of taught defects, for example, an order of defect ID or an order which is consecutive in each defect kind is conceivable. Furthermore, not only the method of changing the taught defect for which image processing results are displayed by using the button 1204 or 1205 on the GUI, but also a method of changing the taught defect by input such as key input from a keyboard, a wheel operation of a mouse, and right click is also conceivable.

Reference numeral 1207 denotes a defect kind in the taught defect for which image processing results are being displayed. Information (such as DOI setting or a feature quantity) concerning a taught defect may be displayed in 1207.

Reference numeral 1208 denotes a composite area of defect recognition results selected by the user, for example, a display part, such as a sum area or a product area of defect areas in a plurality of defect recognition results selected by the user. In FIG. 11, three defect recognition results surrounded by a thick frame are selected, and the defect area differs from defect recognition result to defect recognition result. Composite areas such as sum areas or product areas in these different areas are displayed to be superimposed on the defect image. As for the display of the composite area, the composite area may be displayed automatically by selecting a plurality of defect recognition results. Or the composite area may be displayed by selecting a plurality of defect recognition results and then pressing a composition button (not illustrated). By the way, even in the case where there are results indicating the same area in the defect areas in the selected defect recognition results, application is possible. Furthermore, as for the display of the composite area, the composite area may be displayed by a line, or the defect recognition results may be displayed side by side with a defect image, or may be displayed in a different GUI window, in the same way as 1203. Various kinds of setting are possible. Furthermore, the ideal output may be also displayed to be superimposed on a defect image, may be displayed side by side with the defect image, or may be displayed in a different GUI window, together with the defect recognition result. By the way, the area subjected to defect recognition and the ideal output may be displayed with a changed color, line thickness, line kind, or the like, or may be displayed by painting out the area with a color different from a background color or a semitransparent color having a color different from the background color.

Reference numeral 1209 denotes defect images displayed in a line. In an example shown in FIG. 11, an SE image, an L image, and an R image are displayed in a line. Furthermore, the display is not restricted to defect images, but non-defective article images may be displayed.

Reference numeral 1210 denotes a combo box for specifying an image to be superimposed on 1201. In the example shown in FIG. 11, an SE image is selected and specifying an L image, an R image and the like is possible. However, the displayed image is not restricted to them, a mixture image of an L image, an R image and the like may be displayed.

By the way, in FIG. 11, an example of input of an ideal defect area in defect recognition is shown. However, it can be applied to an input form of an ideal output in interconnection recognition and other image processing.

FIG. 12 shows an example in which image processing results are divided and displayed according to the value of the specific image processing parameter (specific parameter) in the image processing parameter set as regards the GUI for inputting the ideal output shown in FIG. 11. By the way, in the example shown in FIG. 12, a GUI for inputting ideal processing results in interconnection recognition is shown. It is supposed that an image processing parameter set of a determination object has five image processing parameters (parameters 1 to 5) and a value of 1 or 2 can be set in each of the five image processing parameters (the number of settable levels is 2).

Reference numeral 1301 denotes an interconnection recognition result. In the present example, a recognized interconnection area is displayed with a white image and other areas are displayed with a black image, i.e., the areas are displayed with a bi-valued image. By the way, 1301 may be displayed by lines to be superimposed on a defect image or a non-defective article image in the same way as 1201. Or the interconnection recognition results may be displayed side by side with a defect image or a non-defective article image, or may be displayed in a different GUI window. Various kinds of change are possible. Furthermore, the ideal output may also be displayed to be superimposed on a defect image or a non-defective article image, displayed side by side with the defect image or the non-defective article image, displayed in a different GUI window, together with the interconnection recognition result. By the way, the area subjected to interconnection recognition and the ideal output may be displayed with a changed color, line thickness, line kind, or the like, or may be displayed by painting out the area with a color different from a background color or a semitransparent color having a color different from the background color.

Reference numeral 1302 denotes values of specific parameters. In an example shown in FIG. 12, specific parameters are a parameter 1 and a parameter 2. Reference numeral 1302 denotes an example in the case where both values of specific parameters are 1. Reference numeral 1303 denotes a list of interconnection recognition results in an image processing parameter set having values of specific parameters displayed in 1302. At this time, image processing parameters (parameters 3 to 5) other than the specific parameters have arbitrary values. Each of reference numerals 1304 to 1306 denotes a list of image processing results in an image processing parameter set in which a specific parameter value in the image processing parameter set has a corresponding specific parameter value, in the same way as 1303. By the way, a method of dividing interconnection recognition results using an image processing parameter set defined in the orthogonal array table according to the value of the specific parameter and displaying the divided results in 1303 to 1306 is also conceivable. Image processing results displayed in 1303 to 1306 are not restricted to only image processing results in the image processing parameter described in the orthogonal array table, but they may be image processing results in an image processing parameter set which is previously defined by the user, or may be image processing results in an image processing parameter set which is set randomly. Furthermore, as for the image processing results displayed in 1303 to 1306, image processing results may be displayed with respect to all image processing parameter sets defined in the orthogonal array table, or may be displayed with respect to only a part of them. The list of image processing results in 1303 to 1306 is not restricted to the size order of the recognized area, but the list may be displayed in the order of image processing parameter value in the image processing parameter set or the list may be displayed in the order of the value of a feature quantity (such as, in interconnection recognition, coarseness of a recognized circuit pattern) of image processing result.

Reference numeral 1307 denotes an interconnection recognition result used as the selected ideal output. In the example shown in FIG. 12, selected interconnection recognition results are displayed emphatically with thick frames for the user to be able to discriminate them. One or a plurality of interconnection recognition results used as the ideal output are selected from the interconnection recognition results in 1303 to 1306, for each taught defect (which means, in the interconnection recognition, a non-defective article image). By the way, it is also possible not to select even one ideal processing result. Processing such as excluding defects (which means, in the interconnection recognition, a non-defective article image) having image processing results displayed in the GUI window from taught defects (i.e., keeping from coincidence degree calculation) may be conducted by selecting nothing at all.

Reference numeral 1308 denotes a composite area of interconnection recognition results selected by the user, for example, a display part, such as a sum area or a product area of interconnection areas in a plurality of interconnection recognition results selected by the user. In FIG. 12, seven interconnection recognition results are selected, and the interconnection area differs from interconnection recognition result to interconnection recognition result. Composite areas such as sum areas or product areas in these different areas are displayed to be superimposed on a non-defective article image. By the way, even in the case where there are results indicating the same area in the interconnection areas in the selected interconnection recognition results, application is possible. Furthermore, the composite area is not always generated by using all selected interconnection recognition results, but also a composite area of interconnection recognition results selected every value of a specific parameter may be displayed or a composite area of interconnection recognition results selected only for a specific value of a specific parameter may be displayed. Furthermore, as for display of the composite area, the composite area may be displayed by a line, or the defect recognition results may be displayed side by side with a defect image or a non-defective article image, or may be displayed in a different GUI window, in the same way as 1203. Furthermore, the ideal output may be also displayed to be superimposed on a defect image (which means, in interconnection recognition, a non-defective article image), may be displayed side by side with the defect image, or may be displayed in a different GUI window together with the interconnection recognition result. By the way, the area subjected to defect recognition and the ideal output may be displayed with a changed color, line thickness, line kind, or the like, or may be displayed by painting out the area with a color different from a background color or a semitransparent color having a color different from the background color.

The display method of image processing results is not restricted to dividing and displaying image processing results according to the value of a specific parameter, but it is also possible to divide and display image processing results according to the kind of the image processing algorithm utilized at the time of image processing. In FIG. 12, an example of input of ideal interconnection areas in interconnection recognition is shown. It can be applied to an input form of an ideal output in defect recognition and other image processing as well. Furthermore, it can be applied in the case where the number of image processing parameters and the number of levels which can be set are different from those in the example shown in FIG. 12.

In the present embodiment, it becomes possible to reduce the trouble of inputting and shorten time required for inputting to cause the user to select an input of an ideal output out of a plurality of candidates.

Heretofore, the invention made by the present inventor has been described concretely on the basis of the embodiments. However, the present invention is not restricted to the embodiments, but it is a matter of course that various changes can be made without departing from the spirit. In the embodiments described here, a function (ADC) of automatically classifying defect images picked up by using a review SEM is taken as an example and a technique for determining image processing parameters which become necessary in defect recognition processing, interconnection recognition, and the like which are concrete processing contents of the function (ADC) has been described. However, the technique for determining image processing parameters can also be applied to other defect observation devices and inspection devices involving processing for recognizing a defect or an interconnection region from the image acquired in this way. For example, in the review SEM, a defect image having a wide visual field (example: several micrometers) is picked up once, then a defect position is recognized by image processing, and an image having a high magnification (having a narrow visual field, example: 0.5 to 0.1 micrometer) around the recognized region is picked up, in order to collect defect images for automatic classification. In the defect recognition processing for the wide visual field image as well, however, it is necessary to set a plurality of image processing parameters such as a threshold in order to recognize a defect region properly. In this case as well, it is possible to determine the image processing parameters by using the image processing parameter determination method described in the present invention. Furthermore, as the defect inspection device, there is not only an inspection device having an image pickup means of an electron beam type such as a review SEM described in the foregoing description, but also an inspection device having an optical image pickup means. In the optical inspection device as well, it is conducted to recognize a defect by setting a plurality of image processing parameters and applying image processing to the acquired image. It becomes possible to determine a plurality of image processing parameters to be set, by using the determination method indicated in the present invention. In the present invention, the case where there are three detectors in the review SEM has been described. In the optical inspection device as well, however, it is possible to provide a plurality of detectors and obtain a plurality of kinds of images by conducting inspection once. Furthermore, it is also possible to acquire a plurality of images from one detector by changing illuminating light or the detection condition. Even when combining a plurality of images with arbitrary ratios in this way and then recognizing a defect by using suitable image processing parameters, it is possible to determine the ratios of images and the image processing parameters by using the image processing parameter determination method according to the present invention.

In addition, effects provided by the present invention will be exemplified hereafter. According to the present invention, it becomes possible to conduct setting of the image processing parameter set sensibly by causing information which is input to the system in adjustment of a large number of image processing parameters to be an ideal image processing result instead of parameter values. Furthermore, since the image processing parameter set is determined automatically, it becomes possible to save the user the trouble of trial and error. Furthermore, in the automatic determination of the parameter set, results of all image processing parameter sets are not found by image processing, but image processing is conducted only on a small number of restricted image processing parameter sets and on the basis of the result, processing results of image processing parameter sets other than the small number of restricted image processing parameter sets are estimated. Accordingly, it becomes possible to make the processing fast as compared with conducting image processing on all parameter sets. As a result, it becomes possible according to the present invention to set an image processing parameter set required to classify defect kinds, easily and fast.

REFERENCE SIGNS LIST

101: electron source, 102: acceleration electrode, 103: focusing lens, 104: deflector, 105: objective lens, 106: sample, 107: stage, 108: primary electrons, 109: secondary electrons, 110: detector, 111: detector, 112: digitization means, 113: general control unit, 114: storage unit, 115: defect information storage unit, 116: recipe storage unit, 118: operation unit, 119: defect recognition unit, 120: interconnection recognition unit, 121: feature quantity calculation unit, 122: classification unit, 123: input/output unit, 124: automatic determination unit, 130: SEM image acquisition unit, 131: signal processing unit. 132: bus, 201: automatic determination recipe generation unit, 202: coincidence degree calculation unit, 203: coincidence degree estimation unit, 204: parameter determination unit.

The invention claimed is:

1. A defect observation method for observing a defect of a sample, comprising the steps of:
    picking up a plurality of defect images by using an electron microscope on the basis of previously detected defect coordinates of a sample;
    processing a teaching defect image selected out of the plurality of picked up defect images, by using respective conditions of a first plurality of image processing parameter sets which are previously set, and extracting a plurality of defect areas respectively corresponding to the first plurality of image processing parameter sets;
    comparing an ideal defect area which is set to correspond to the selected teaching defect image with the extracted plurality of defect areas and calculating a coincidence degree every the plurality of defect areas;
    calculating an estimated value of coincidence degree with respect to each of a second plurality of image processing parameter sets different from the first plurality of image processing parameter sets which are previously set, by using the coincidence degree calculated for each of the plurality of defect areas;
    selecting one or a plurality of image processing parameter sets out of the first plurality of image processing parameter sets which are previously set and the second plurality of image processing parameter sets on the basis of the calculated plurality of coincidence degrees and estimated values of coincidence degree; and
    conducting image processing on the plurality of defect images picked up with the electron microscope by using the selected image processing parameter set and classifying the defect of the sample on the basis of the defect images subjected to the image processing.

2. The defect observation method according to claim 1, wherein the step of classifying the defect of the sample comprises the steps of:
    extracting defect areas of the plurality of defect images picked up with the electron microscope by using the selected image processing parameter set; and
    calculating a feature quantity in the extracted defect areas of the defect images and classifying the defect of the sample on the basis of the calculated feature quantity.

3. The defect observation method according to claim 1, wherein at the step of calculating an estimated value of coincidence degree, an estimated value of coincidence degree is obtained by estimating a coincidence degree with respect to the second plurality of image processing parameter sets on the basis of distribution of a coincidence degree calculated for each of the plurality of defect areas.

4. The defect observation method according to claim 1, wherein the first plurality of image processing parameter sets which are previously set are less in number than the second plurality of image processing parameter sets.

5. The defect observation method according to claim 1, wherein the first plurality of image processing parameter sets which are previously set are sets specified by a user or sets which are selected and set randomly.

6. The defect observation method according to claim 1, wherein the ideal defect area is an area which is set by a user on the basis of the selected teaching defect image displayed on a GUI screen.

7. The defect observation method according to claim 1, wherein the ideal defect area is an area selected out of image processing results processed by using image processing parameter sets which are specified by a user or selected randomly.

8. The defect observation method according to claim 1, wherein the teaching defect image is an image selected automatically by using information of a defect kind based upon the plurality of picked up defect images as reference.

9. A defect observation method for observing a defect of a sample, comprising the steps of:
picking up a plurality of defect images and non-defective article images by using an electron microscope on the basis of previously detected defect coordinates of a sample;
processing a teaching interconnection image selected out of the picked up non-defective article images, by using respective conditions of a first plurality of combinations of image processing parameter sets and image processing algorithms which are previously set, and extracting a plurality of interconnection areas respectively corresponding to the first plurality of image processing parameter sets and image processing algorithms;
comparing an ideal interconnection area which is set to correspond to the selected teaching interconnection image with the extracted plurality of interconnection areas and calculating a coincidence degree for each of the plurality of interconnection areas;
calculating an estimated value of coincidence degree with respect to each of a second plurality of combinations of image processing parameter sets and image processing algorithms different from the first plurality of combinations of image processing parameter sets and image processing algorithms which are previously set, by using the coincidence degree calculated for each of the plurality of interconnection areas;
selecting one or a plurality of image processing parameter sets and image processing algorithms out of the first plurality of combinations of image processing parameter sets and image processing algorithms which are previously set and the second plurality of combinations of image processing parameter sets and image processing algorithms on the basis of the calculated plurality of coincidence degrees and estimated values of coincidence degree; and
conducting image processing on the plurality of defect images picked up with the electron microscope by using the selected image processing parameter sets and image processing algorithms and classifying the defect of the sample on the basis of the defect images subjected to the image processing.

10. The defect observation method according to claim 9, wherein the first plurality of combinations of image processing parameter sets and image processing algorithms which are previously set are less in number than the second plurality of combinations of image processing parameter sets and image processing algorithms.

11. The defect observation method according to claim 9, wherein the ideal interconnection area is an area selected out of image processing results processed by using combinations of image processing parameter sets and image processing algorithms which are specified by a user or selected randomly.

12. A defect observation method in a defect observation device including an image acquisition unit for acquiring a defect image of a sample, a storage unit, and an input/output unit, an operation unit which is supplied with image information from the image acquisition unit and which conducts image processing for recognizing a defect on the sample and classifying a defect kind, on the image information on the sample by using a previously set image processing parameter set, and an automatic determination unit for automatically determining setting candidates of the image processing parameter set, the defect observation method comprising the steps of:
selecting, in the input/output unit, one or a plurality of representative defects;
inputting, in the operation unit, ideal outputs for the representative defects of the image processing;
calculating coincidence degrees between output results obtained by conducting the image processing on the representative defects in a small number of image processing parameter sets and the ideal outputs;
calculating estimated values of coincidence degrees with respect to image processing parameter sets which are not included in the small number of image processing parameter sets, on the basis of the coincidence degrees;
determining one set or a plurality of sets of setting candidates of the image processing parameter set on the basis of the estimated values of coincidence degrees and the coincidence degrees; and
displaying, in the input/output unit, the image processing parameter set of the setting candidate and output results obtained by conducting the image processing on the representative defects in the image processing parameter set of the setting candidate.

13. The defect observation method according to claim 12, wherein the ideal outputs are selected out of image processing results processed by using image processing parameter sets which are specified by a user or selected randomly.

14. The defect observation method according to claim 12, wherein if a plurality of image processing algorithms of the image processing are prepared, the automatic determination unit automatically determines setting candidates of combinations of image processing parameter sets and corresponding image processing algorithms.

15. The defect observation method according to claim 14, wherein the ideal outputs are selected out of image processing results processed by using combinations of image processing parameter sets and corresponding image processing algorithms which are specified by a user or selected randomly.

16. The defect observation method according to claim 12, wherein at the step of calculating coincidence degrees and the step of determining setting candidates, there are a plurality of processing modes which change in processing time or determined setting candidates.

17. The defect observation method according to claim 12, wherein images of the representative defects comprise a mixture image of a plurality of images.

18. The defect observation method according to claim 12, wherein a parameter included in the image processing parameter set comprises a mixture ratio of images.

19. The defect observation method according to claim 12, wherein at the step of determining setting candidates, information of DOI is utilized.

20. The defect observation method according to claim 12, wherein if results of the image processing using the determined setting candidate are insufficient, then addition and deletion of representative defects are conducted on the basis of the results of the image processing using the determined setting candidate, and determination of the setting candidate in the automatic determination unit is conducted repeatedly.

* * * * *